(12) United States Patent
Grammenos et al.

(10) Patent No.: US 6,232,317 B1
(45) Date of Patent: May 15, 2001

(54) BISIMINO-SUBSTITUTED PHENYL COMPOUNDS AND THEIR USE AS PESTICIDES

(75) Inventors: Wassilios Grammenos, Ludwigshafen; Herbert Bayer; Hubert Sauter, both of Mannheim; Thomas Grote, Schifferstadt; Andreas Gypser, Mannheim; Bernd Müller, Frankenthal; Arne Ptock, Ludwigshafen; Franz Röhl, Schifferstadt; Norbert Götz, Worms; Eberhard Ammermann, Heppenheim; Volker Harries, Frankenthal; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/463,435

(22) PCT Filed: Jul. 20, 1998

(86) PCT No.: PCT/EP98/04488
§ 371 Date: Jan. 27, 2000
§ 102(e) Date: Jan. 27, 2000

(87) PCT Pub. No.: WO99/06379
PCT Pub. Date: Feb. 11, 1999

(30) Foreign Application Priority Data

Jul. 30, 1997 (DE) .................................................. 19732846

(51) Int. Cl.[7] ........................ A01N 43/653; A01N 43/76; C07D 249/12; C07D 261/12; C07D 413/04

(52) U.S. Cl. .......................... 514/256; 514/340; 514/374; 514/378; 514/380; 514/383; 514/384; 514/406; 548/215; 548/240; 548/243; 548/263.2; 548/264.6; 548/272.1; 548/272.4; 548/333; 548/364.1; 548/365.7

(58) Field of Search .................................. 514/380, 384; 548/243, 263.2, 264.6

(56) References Cited

U.S. PATENT DOCUMENTS 5,194,662  3/1993  Brand ...................... 514/357

FOREIGN PATENT DOCUMENTS

| 14160/95 | 8/1995 | (AU) . |
| 40 20 384 | 1/1992 | (DE) . |
| 95/14009 | 5/1995 | (WO) . |
| WO 95/21154 * | 8/1995 | (WO) . |
| 97/02255 | 1/1997 | (WO) . |
| WO 97/02255 * | 1/1997 | (WO) . |
| 98/23155 | 6/1998 | (WO) . |
| WO 98/23155 * | 6/1998 | (WO) . |

* cited by examiner

Primary Examiner—Jane C. Oswecki
(74) Attorney, Agent, or Firm—Keil & Weinkauf

(57) ABSTRACT

Imino-substituted phenyl compounds of the formula I

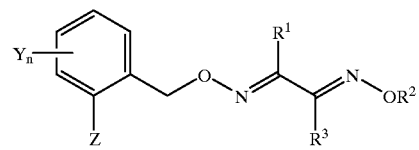

I where the substituents have the following meanings:
z is a group A or B

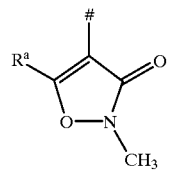

A

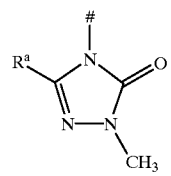

B where
# denotes the bond with the phenyl ring and
$R^a$ is halogen, alkyl or alkoxy;
y is halogen, alkyl, haloalkyl or alkoxy;
n is 0, 1 or 2, it being possible for the radicals Y to be different if n=2;
$R^1$ is halogen, haloalkyl or alkoxy;
$R^2$ is alkyl, haloalkyl, alkenyl, haloalkenyl, alkynyl or haloalkynyl;
$R^3$ is cyano, alkyl, haloalkyl, alkoxy, cycloalkoxy, alkoxyalkyl;
unsubstituted or substituted cycloalkyl, aryl, aryloxy or arylmethylene, heteroaryl, heterocyclyl,
$C(R^{3a})=N-OR^{3b}$ or $C(R^{3a})=CR^{3c}R^{3d}$, where
$R^{3a}$, $R^{3b}$, $R^{3c}$, $R^{3d}$ independently of one another are hydrogen, alkyl or unsubstituted or substituted phenyl,
processes for their preparation, and their use.

10 Claims, No Drawings

BISIMINO-SUBSTITUTED PHENYL COMPOUNDS AND THEIR USE AS PESTICIDES

This application is a 371 of PCT/EP98/04488 filed Jul. 20, 1998.

The present invention relates to imino-substituted phenyl compounds of the formula I

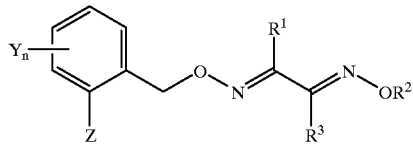

where the substituents have the following meanings:
z is a group A or B

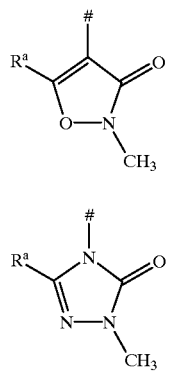

where
\# signifies the bond with the phenyl ring and
$R^a$ is halogen, $C_1$–$C_4$-alkyl or $C_1$–$C_4$-alkoxy;
Y is halogen, $C_1$–$C_4$-alkyl, $C_1$–$C_4$-haloalkyl or $C_1$–$C_4$-alkoxy;
n is 0, 1 or 2, it being possible for the radicals Y to be different if n=2;
$R^1$ is halogen, $C_1$–$C_4$-haloalkyl or $C_1$–$C_4$-alkoxy;
$R^2$ is $C_1$–$C_4$-alkyl, $C_1$–$C_4$-haloalkyl, $C_3$–$C_4$-alkenyl, $C_3$–$C_4$-haloalkenyl, $C_3$–$C_4$-alkynyl or $C_3$–$C_4$-haloalkynyl;
$R^3$ is cyano, $C_1$–$C_6$-alkyl, $C_1$–$C_6$-haloalkyl, $C_1$–$C_6$-alkoxy, $C_3$–$C_6$-cycloalkoxy, $C_2$–$C_6$-alkoxyalkyl;
$C_3$–$C_6$-cycloalkyl, which can be partially or fully halogenated and/or have attached to it one to three $C_1$–$C_4$-alkyl groups;
phenyl which, in turn, can be partially or fully halogenated and/or have attached to it one to three of the following groups: cyano, nitro, $C_1$–$C_4$-alkyl, $C_1$–$C_4$-haloalkyl, $C_1$–$C_4$-alkoxy and $C_1$–$C_4$-haloalkoxy;
aryl, aryloxy or arylmethylene which can be partially or fully halogenated in the aryl moiety and/or can have attached to it one to three of the following radicals: cyano, nitro, $C_1$–$C_4$-alkyl, $C_1$–$C_4$-haloalkyl, $C_1$–$C_4$-alkoxy and $C_1$–$C_4$-haloalkoxy;
unsubstituted or substituted heteroaryl, unsubstituted or substituted heterocyclyl, $C(R^{3a})$=N—$OR^{3b}$ or $C(R^{3a})$=$CR^{3c}R^{3d}$, where
$R^{3a}$, $R^{3b}$, $R^{3c}$, $R^{3d}$ independently of one another are hydrogen, $C_1$–$C_6$-alkyl or unsubstituted or substituted phenyl.

In addition, the invention relates to processes and intermediates for the preparation of the compounds I, and to compositions and to the use of the compounds I for controlling harmful fungi and animal pests.

4-phenyl-2,3-dihydroisoxazolones and 4-phenyl-2,4-dihydrotriazolones having a methyleneoximino group in the ortho position are disclosed in WO-A 95/14,009 and those which have a bisoxime ether group in the ortho position are disclosed in WO-A 97/02,255.

α-Phenylacrylic acid derivatives and α-phenyl-α-methoximinoacetic acid derivatives having an oxime ether group in the ortho position are described in DE-A 40 20 384 and such derivatives which have a bisoxime ether group are described in WO-A 95/21,154.

The compounds described in the abovementioned documents are suitable as crop protection agents against harmful fungi and, in some cases, against animal pests.

However, their action is not satisfactory in many cases. It is an object of the present invention to find compounds with an improved activity.

We have found that this object is achieved by the phenyl compounds of the formula I. We have furthermore found intermediates and processes for the preparation of the compounds I and the use of the compounds I and compositions comprising them for controlling harmful fungi and animal pests. The fungicidal action is preferred.

The compounds of the formula I differ from the compounds disclosed in the abovementioned document WO-A 97/02,255 in context with the substitution of the oximino group by the radical
$R^1$ which is bonded to a double bond and which has specific features. In contrast to the known compounds, the compounds of the formula I have an improved activity against harmful fungi and animal pests.

The compounds of the formula I per se can be obtained by methods similar to those described in WO-A 95/14,009, WO-A 97/02,255, and WO-A 95/21,153.

The compounds I can be obtained in various ways, it being irrelevant for the synthesis whether the group Z or the oxime ether group is synthesized first. For reasons of better clarity, the term Z\# is used for the radical Z or a suitable precursor of this radical, and E\# is used for the oxime ether group or a suitable precursor thereof, in the reactions described hereinbelow.

Compounds I where $R^1$ is halogen are especially advantageously obtained by first converting a carboxylic ester IIIa with hydroxylamine to give the corresponding hydroxambic acid IIIb, subsequently reacting IIIb with a benzyl compound IIa\# to give the corresponding hydroxambic ester IVa\# and converting IVa\# with a halogenating agent [HAL] to give I\# [cf. DE-Anm. No. 197 08 940.2].

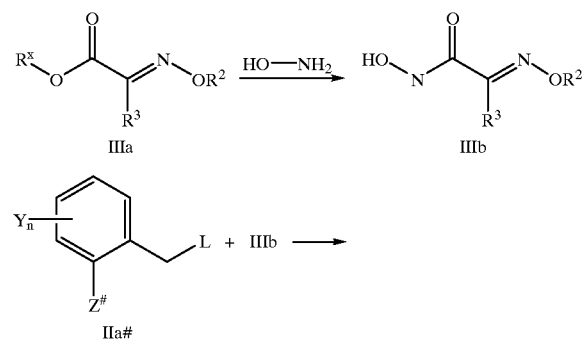

-continued

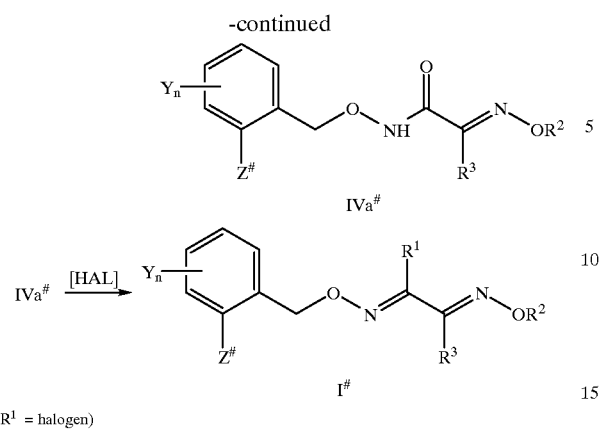

(R¹ = halogen)

R$^x$ in formula IIIa is the radical of a customary leaving group. Customary leaving groups for the purposes of the present reaction are to be understood as meaning especially the following groups: $C_1$–$C_4$-alkyl (especially methyl or ethyl) or phenyl.

L in formula IIa# is a nucleophile leaving group. For the purposes of this reaction, this is to be understood as meaning especially the following: halogen or alkyl- or arylsulfonate, especially chlorine, bromine, iodine, mesylate, tosylate and triflate.

1. The reaction of the carboxylic ester IIIa with hydroxylamine is normally carried out at from −20° C. to 50° C., preferably 0° C. to 20° C., in an inert organic solvent, preferably in the presence of a base (cf. Lit. Houben-Weyl, 4th Edition, Vol. E5, p. 1141 et seq.).

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, and also dimethyl sulfoxide, dimethyl formamide and dimethylacetamide, especially preferably alcohols such as methanol and ethanol. Mixtures of these can also be used.

Bases which are suitable are, generally, inorganic compounds such as alkali metal hydroxide and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal carbonates and alkaline earth metal carbonates such as lithium carbonate and calcium carbonate, and alkali metal alkoxides and alkaline earth metal alkoxides such as sodium methoxide, sodium ethoxide, potassium ethoxide, potassium tert-butoxide and dimethoxymagnesium, and furthermore organic bases, eg. tertiary amines such as trimethylamine, triethylamine, triisopropylethylamine and N-methylpiperidine, pyridine substituted pyridines such as collidine, lutidine and 4-dimethylaminopyridine, and by bicyclic amines. Alkali metal hydroxides such as sodium hydroxide and potassium hydroxide, and alkali metal alkoxides such as sodium methoxide and sodium ethoxide, are especially preferred.

The bases are generally used in equimolar amounts or in an excess.

The starting materials are generally reacted with each other in equimolar amounts. It may be advantageous for the yield to employ hydroxylamine in an excess based on IIIa.

Those carboxylic esters IIIa required for the preparation of the compounds I which are not already known from the literature [DE-A 28 08 317; DE-A 22 65 234; J. Chem. Soc. PT 1 (1975), 2340 et seq.; Chem. Ber. 16 (1883), 2987 et seq.; J. Org. Chem. 37 (1972), 139] can be prepared in accordance with the literature cited.

2. The reaction of the hydroxambic acid IIIb with the benzyl compound IIa# is normally carried out at from 0° C. to 130° C., preferably 10° C. to 60° C., in an inert organic solvent in the presence of a base [cf. Liebigs Ann. Chem. 10 (1992), 997 et seq.; Synth. Commun. 19 (1989), 339 et seq.]. Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide, dimethyl formamide and dimethyl acetamide, especially preferably tetrahydrofuran, acetonitrile and dimethyl formamide. Mixtures of these can also be used.

Bases which are suitable are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate, potassium carbonate and calcium carbonate, and alkali metal hydrogen carbonates such as sodium hydrogen carbonate, organometallic compounds, in particular alkali metal alkyls such as methyllithium butyllithium and phenyllithium, alkylmagnesium halides such as methylmagnesium chloride, and alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and bicyclic amines. Sodium methoxide, potassium carbonate and sodium hydride are especially preferred.

The bases are generally used in equimolar amounts, in an excess or, if appropriate, as the solvent.

The starting materials are generally reacted with each other in equimolar amounts. It may be advantageous for the yield to employ IIIb in an excess based on IIa#.

Those benzyl compounds required for this reaction which are not already known from the literature cited at the outset can be prepared in accordance with this literature.

3. This halogenation of the hydroxambic esters IVa# is normally carried out at from −20° C. to 100° C., preferably −10° C. to 80° C., in an inert organic solvent [cf. Houben-Weyl, 4th Ed., Vol. E5, p. 631 et seq.; J. Org. Chem. 36 (1971), 233; Synthesis 9 (1991), 750 et seq.; Tetrahedron 52(1) (1996), 233 et seq.].

Suitable halogenating agents in this reaction are the customary inorganic and organic halogenating agents, eg.

thionyl chloride, oxalyl chloride, phosphorus tribromide, phosphorus trichloride, phosphorus pentachloride, phosphorus oxychloride, phosphorus triiodide, triphenylphosphine/$CCl_4$, triphenylphosphine/$CBr_4$, triphenylphosphine/iodine, preferably thionyl chloride, or the abovementioned triphenylphosphine reagents.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, ketones such as acetone, methyl ethyl ketone, diethyl ketone and tert-butyl methyl ketone, and also dimethyl sulfoxide, dimethyl formamide and dimethyl acetamide, especially preferably acetonitrile, toluene and tetrahydrofuran. Mixtures of these can also be used.

The halogenating agents are generally employed in at least equimolar amounts. It may be advantageous for the yield to employ them in an excess of up to 10 mol based on 1 mol of IVa#, preferably up to 5 mol, in particular up to 3 mol.

4. Alternatively, the compounds IVa# can also be obtained by reacting a carboxylic acid IIIc with a benzyl hydroxylamine IIb#.

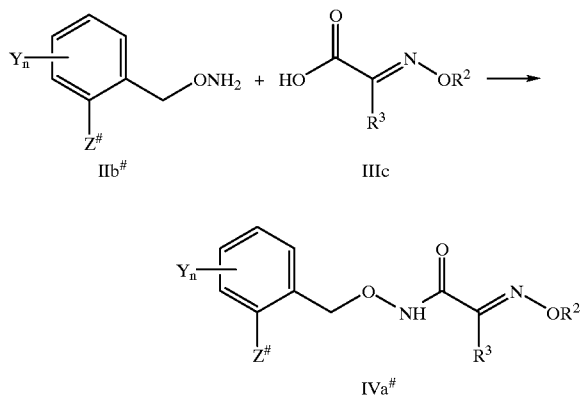

This reaction is normally carried out at from −10° C. to 120° C., preferably 0° C. to 50° C., in an inert organic solvent in the presence of an activating reagent [cf. Houben-Weyl, 4th Ed., Vol. E5, p. 1141 et seq.; J. Antibiot. 39 (1986), 1382].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide, dimethyl formamide and dimethyl acetamide, especially preferably tetrahydrofuran and methylene chloride. Mixtures of these can also be used.

Suitable activation reagents are acid halide formers such as phosgene, phosphorus tribromide, phosphorus trichloride, phosphorus pentachloride, phosphorus oxychloride, thionyl chloride or oxalyl chloride; anhydride formers such as ethyl chloroformate or methanesulfonyl chloride; carbodiimides such as N,N'-dicyclohexylcarbodiimide, or other customary agents such as N,N'-carbonyldiimidazole or triphenylphosphine in $CCl_4$. Thionyl chloride, oxalyl chloride and N,N'-carbonyldiimidazole are especially preferred.

The activation reagents are generally employed in equimolar amounts or in an excess.

The starting materials are generally reacted with each other in equimolar amounts. It may be advantageous for the yield to employ IIIc in an excess based on IIb#.

The carboxylic acids IIIc required for this reaction which are not already known from the literature [J. Pharm. Sci. 57 (1968), 688 et seq.; DE-A 22 23 375; DE-A 22 65 234] can be prepared in accordance with the literature cited.

5. In addition, the compounds IVa# are also obtained by reacting a carboxylic ester of the formula IIIa with the benzylhydroxylamine IIb# under the conditions described for the reaction of IIIa to IIIb.

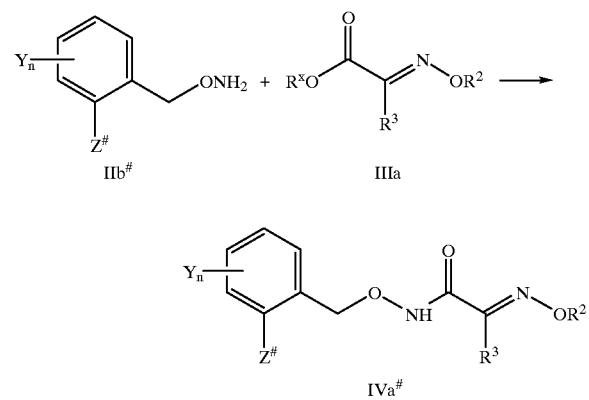

In another process, the compounds I are obtained advantageously by converting an amide oxime IIId with a benzyl compound IIa# into the corresponding compound of the formula IVb# and exchanging the amino group of IVb# for halogen via a diazotization reaction.

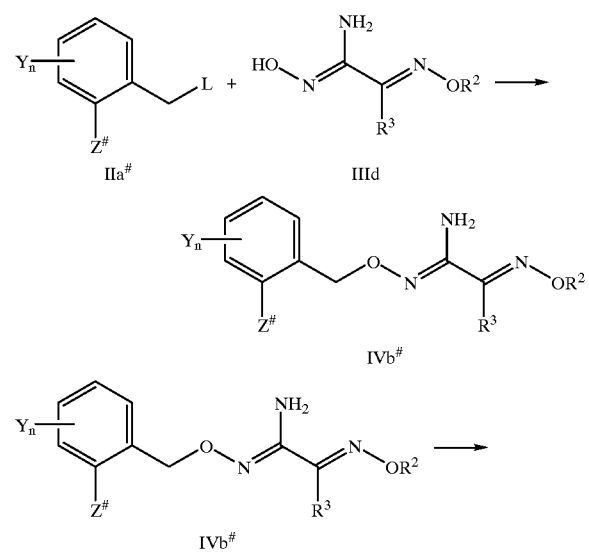

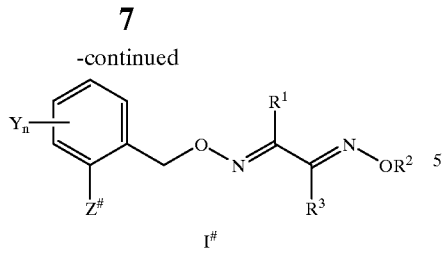

($R^1$ = halogen)

The reaction of the amide oxime IIId with the benzyl compound IIa# is normally carried out at from 0° C. to 130° C., preferably 10° C. to 60° C., in an inert organic solvent in the presence of a base [cf. Lit. Heterocycles 36 (1993), 1027 et seq.].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide, dimethyl formamide and dimethyl acetamide, especially preferably tetrahydrofuran, acetonitrile and dimethyl formamide. Mixtures of these can also be used.

Bases which are suitable are, generally, inorganic compounds such as alkali metal hydroxide and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate, potassium carbonate and calcium carbonate, and alkali metal hydrogen carbonates such as sodium hydrogen carbonate, organometallic compounds, in particular alkali metal alkyls such as methyllithium butyllithium and phenyllithium, alkylmagnesium halides such as methylmagnesium chloride, and alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and bicyclic amines. Sodium methoxide, potassium carbonate and sodium hydride are especially preferred.

The bases are generally used in equimolar amounts or in an excess.

The starting materials are generally reacted with each other in equimolar amounts. It may be advantageous for the yield to employ IIId in an excess based on IIa#.

Those amide oximes IIId required for the preparation of the compounds I which are not already known from the literature [DE-A 44 42 732; Gazz. Chim. Ital. 55 (1925), 327] can be prepared in accordance with the literature cited.

6. The diazotization and halogenation of IVb# to I# is normally carried out at from −20° C. to 50° C., preferably 0° C. to 20° C., in water or in an aqueous inert organic solvent [cf. Lit. J. Org. Chem. 45 (1980), 4144 et seq.; Chem. Ber. 26 (1893), 1567 et seq.].

The halogenating agents used in this reaction are hydrogen fluoride, hydrogen chloride, hydrogen bromide and hydrogen iodide, in particular hydrogen chloride.

The halogenating agents are generally used in an excess or, if appropriate, as the solvent.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide, dimethyl formamide and dimethyl acetamide, especially preferred are, in addition to water, mixtures of dioxane and water and/or tetrahydrofuran and water.

The benzyl compounds IIa# required for the preparation of the compounds I are known from the literature [cf. WO-A 97/02,255]. They can be obtained via the following synthesis route:

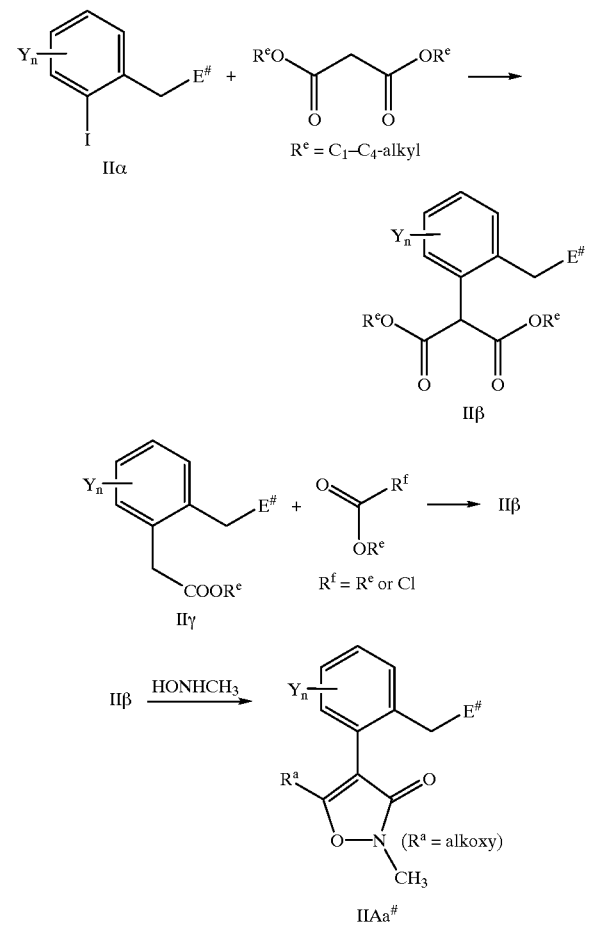

Compounds of the formula IIAa# in which $R^a$ is alkyl are obtained from the corresponding phenylacetic esters IIγ by the route known from U.S. Pat. No. 4,952,573.

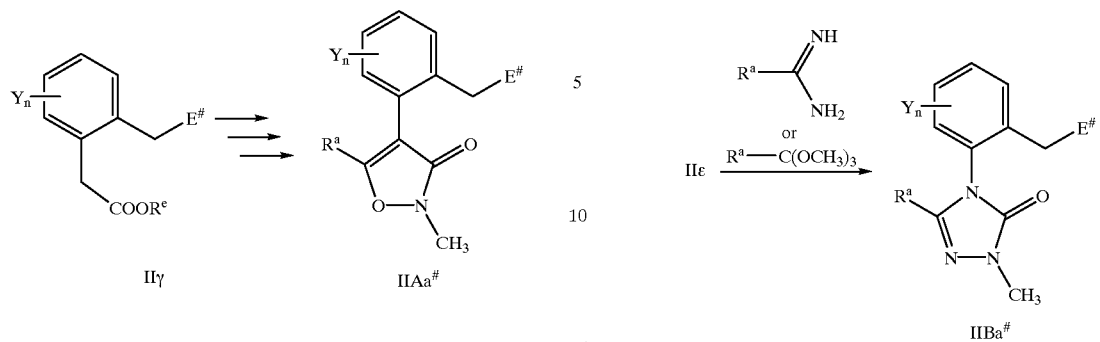

The benzyl compounds IIB# required for preparing the compounds IB in which $R^a$ is halogen or alkoxy are known from the literature [cf. WO-A 97/02,255], or they can be obtained by the methods given in the literature cited. They can be obtained by the following synthesis route:

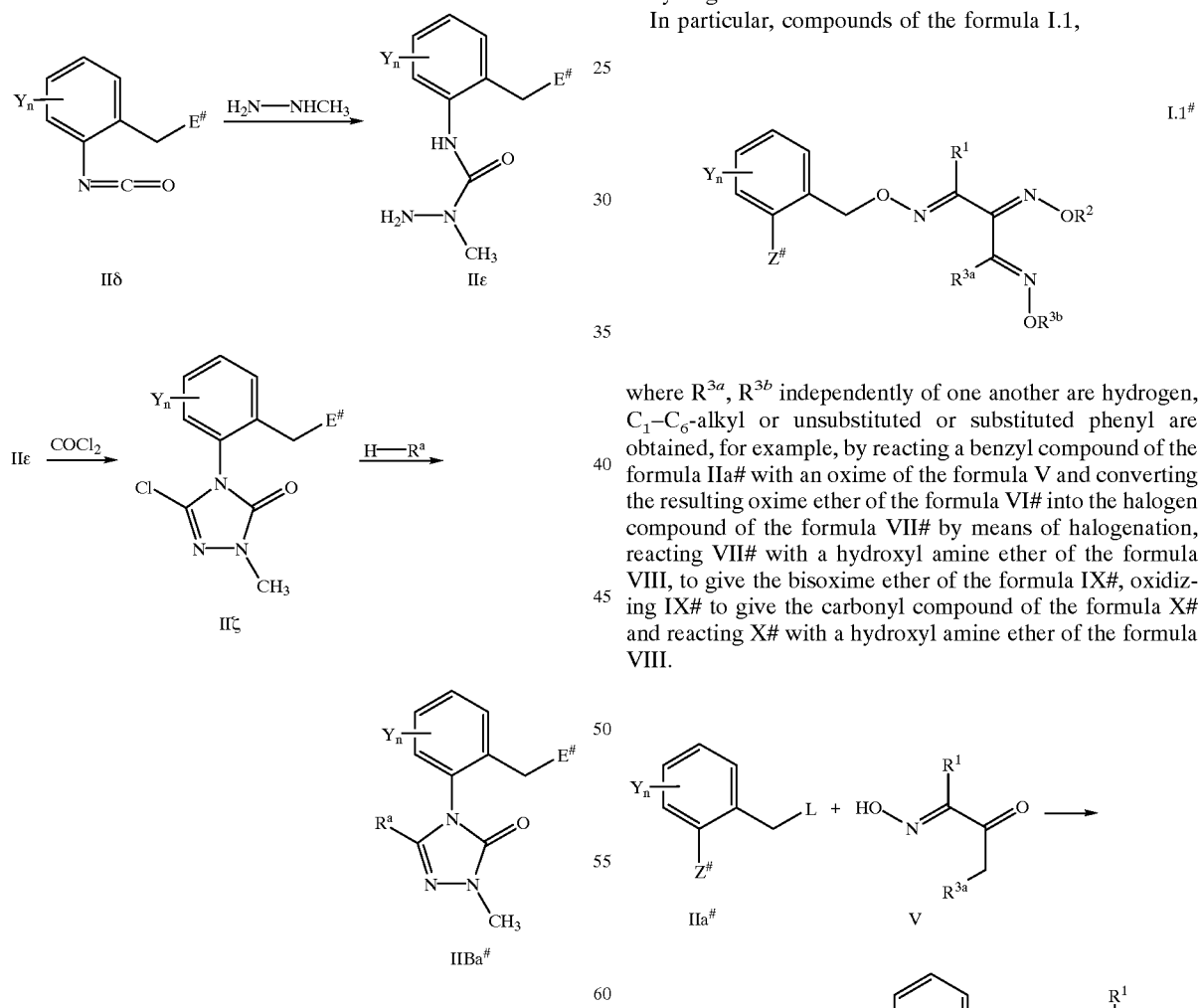

The benzyl compounds IIB# required for preparing the compounds IB in which $R^a$ is alkyl are known from the literature [cf. WO-A 96/36,229], or they can be obtained by the methods given in the literature cited. They can be obtained by reacting the carbamates of the formula IIε with orthoesters:

This route is not only suitable for preparing the benzyl compounds IIa#, but, in principle, suitable for synthesizing the groups A or B at any stage of the synthesis of the oxime ether group E#. The group X is especially preferably synthesized at the stage of the compounds IIα or IIδ, where E# is hydrogen.

In particular, compounds of the formula I.1, where $R^{3a}$, $R^{3b}$ independently of one another are hydrogen, $C_1$–$C_6$-alkyl or unsubstituted or substituted phenyl are obtained, for example, by reacting a benzyl compound of the formula IIa# with an oxime of the formula V and converting the resulting oxime ether of the formula VI# into the halogen compound of the formula VII# by means of halogenation, reacting VII# with a hydroxyl amine ether of the formula VIII, to give the bisoxime ether of the formula IX#, oxidizing IX# to give the carbonyl compound of the formula X# and reacting X# with a hydroxyl amine ether of the formula VIII.

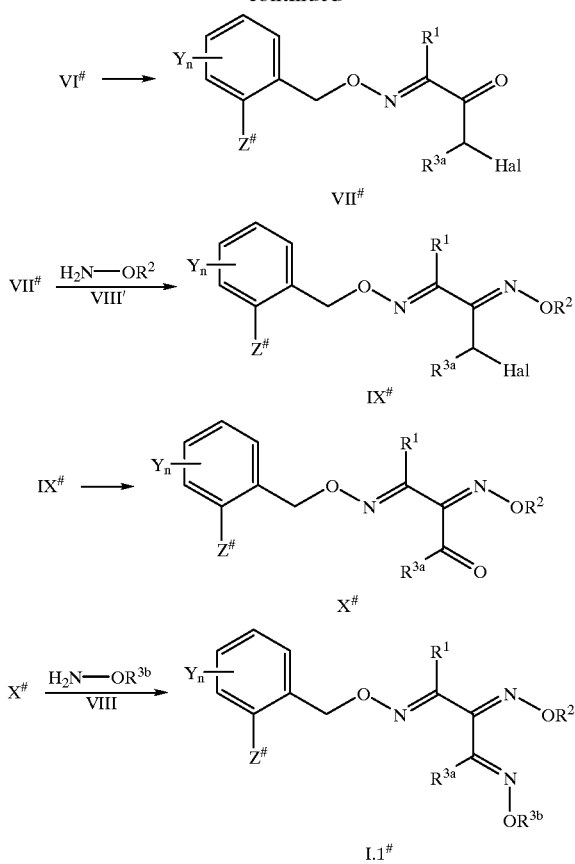

7. The reaction of the benzyl compound IIa# with the oxime of the formula V is carried out in a manner known per se at from −10° C. to 100° C., preferably 10° C. to 85° C., in an inert organic solvent in the presence of a base [cf. WO-A 97/02,255].

Suitable solvents are ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide, dimethyl formamide and dimethyl acetamide, especially preferably tetrahydrofuran, acetonitrile and dimethyl formamide. Mixtures of these can also be used.

Bases which are suitable are, generally, inorganic compounds such as alkali metal hydroxide and alkaline earth metal hydroxides such as lithium hydroxide, sodium hydroxide, potassium hydroxide and calcium hydroxide, alkali metal hydrides and alkaline earth metal hydrides such as lithium hydride, sodium hydride, potassium hydride and calcium hydride, alkali metal carbonates and alkaline earth metal carbonates such as lithium carbonate, potassium carbonate and calcium carbonate, and also alkali metal hydrogen carbonates such as sodium hydrogen carbonate, alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and bicyclic amines. Sodium methoxide, potassium carbonate and sodium hydride are especially preferred.

The bases are generally employed in catalytic amounts, but they can also be used in equimolar amounts, in an excess or, if appropriate, as the solvent.

The starting materials are generally reacted with each another in equimolar amounts. It may be advantageous for the yield to employ V in an excess based on IIa#.

Those oximes of the formula V which are not already known from the literature [cf. WO-A 95/21,153] can be prepared in accordance with the literature cited.

8. The halogenation of the oxime ether VI# is normally carried out at from −10° C. to 80° C., preferably 0° C. to 65° C., in an inert organic solvent, if appropriate in the presence of an acid [cf. J. Org. Chem. (1981), p. 2532; Org. Synth., Vol. 55 (1976), p. 24; Tetrahedron (1970), p. 5611].

Suitable halogenating agents are bromine, chlorine, pyridine*HBr$_3$, CuBr$_2$ and SO$_2$Cl$_2$, in particular bromine, CuBr$_2$ and SO$_2$Cl$_2$. They are generally reacted with each other in equimolar amounts. It may be advantageous for the yield to employ them in a 1.2- to 2.5-fold excess based on the compound IV#.

Suitable solvents are aromatic hydrocarbons such as toluene, o-, m- and p-xylene, halogenated hydrocarbons such as methylene chloride, chloroform and chlorobenzene, and alcohols such as methanol, ethanol n-propanol, isopropanol, n-butanol and tert-butanol, especially preferably cyclohexane, methylene chloride, chloroform, chlorobenzene and methanol. Mixtures of these can also be used.

Acids and acidic catalysts which are used are inorganic acids such as hydrochloric acid, hydrobromic acid and sulfuric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid.

The acids are generally employed in catalytic amounts, but they can also be used in equimolar amounts, in an excess or, if appropriate, as the solvent.

The starting materials are generally reacted with each other in equimolar amounts. It may be advantageous for the yield to employ the halogenating agent in an excess based on IV#.

9. The reaction of the oxime ether VII# with the hydroxylamine ether of the formula VIII' to give the bisoxime ether IX# is carried out in a known manner at from 0° C. to 85° C., preferably 20° C. to 65° C., in an inert organic solvent.

10. The oxidation of the bisoxime ether IX# is carried out in the known manner at from 20° C. to 160° C., preferably 20° C. to 100° C., in an inert organic solvent, if appropriate in the presence of a base [cf. Houben-Weyl, Methoden der organischen Chemie [Methods in organic chemistry], Volume E3, pp. 247–265, Georg Thieme Verlag, Stuttgart 1983].

Suitable oxidants are, for example, N-methylmorpholin-N-oxide, 2-benzoyl-1-trifluoromethanesulfonylhydrazine, trimethylamine-N-oxide and pyridine-N-oxide, in particular N-methylmorpholin-N-oxide, trimethylamine-N-oxide and pyridine-N-oxide.

Suitable bases are, generally, inorganic compounds such as alkali metal hydroxides and alkaline earth metal hydroxides such as lithium hydroxide, sodium hydroxide, potassium hydroxide and calcium hydroxide, alkali metal carbonates and alkaline earth metal carbonates such as lithium carbonate, potassium carbonate and calcium carbonate, and alkali metal hydrogen carbonates such as sodium hydrogen carbonate, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and bicyclic amines. Sodium hydroxide, sodium hydrogen carbonate and potassium carbonate are especially preferred.

The bases are generally employed in catalytic amounts, but they can also be used in equimolar amounts, in an excess or, if appropriate, as the solvent.

The starting materials are generally reacted with each other in equimolar amounts. It may be advantageous for the yield to employ the oxidant in an excess based on IX#.

11. The reaction of the carbonyl compound X# to give trisoxime ether I.1# is normally carried out at from 10° C. to 120° C., preferably 20° C. to 85° C., in an inert organic solvent, if appropriate in the presence of a base [cf. EP-A 386 561].

Suitable solvent are ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, and dimethyl sulfoxide, dimethylformamide and dimethylacetamide, especially preferably methanol and ethanol. Mixtures of these can also be used.

Bases which are suitable are, generally, inorganic compounds such as alkali metal carbonates and alkaline earth metal carbonates such as lithium carbonate, potassium carbonate and calcium carbonate, and also alkali metal hydrogen carbonates such as sodium hydrogen carbonate, alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and bicyclic amines. Sodium hydrogen carbonate, pyridine and triethylamine are especially preferred.

The bases are generally employed in catalytic amounts, but they can also be used in equimolar amounts, in an excess or, if appropriate, as the solvent.

The starting materials are generally reacted with each another in equimolar amounts. It may be advantageous for the yield to employ VIII in an excess based on X#.

Those starting substances of the formula V required for the preparation of the compounds I which are not already known from the literature [J. Org. Chem. (1991), p. 2605; Bull. Soc. Chim. Fr. (1973), p. 1452] can be prepared in accordance with the literature cited.

Compounds of the formula I.2 where $R^{3a}$, $R^{3c}$ and $R^{3d}$ independently of one another are hydrogen, $C_1$–$C_6$-alkyl or unsubstituted or substituted phenyl are obtained, for example, by reacting a carbonyl compound of the formula X# with a phosphorus reagent following the principles of a Wittig reaction to give a compound of the formula I.2#.

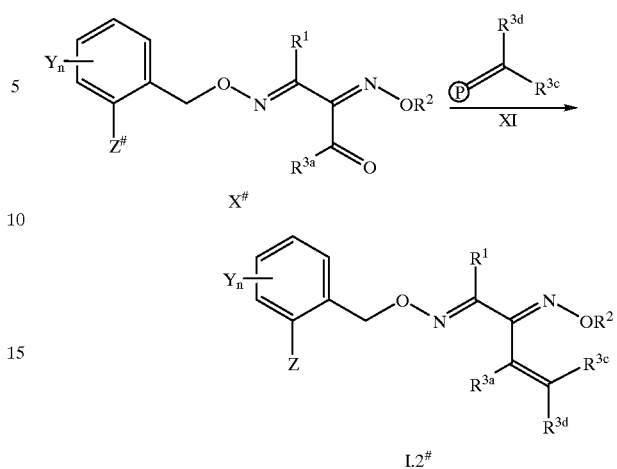

In the above equation, Ⓟ in formula XI is a phosphoranyl radical, for example triphenylphosphoranyl.

12. The Wittig reaction is carried out in a known manner and from −78° C. to 85° C., preferably −10° C. to 65° C., in an inert organic solvent in the presence of a base [cf. EP-A 513 580].

Compounds of the formula I where $R^1$ is $C_1$–$C_4$-alkoxy are obtained, for example, by reacting a compound of the formula I# where $R^1$ is halogen with an alkoxide of the formula XII where M is a cation from amongst the group of the alkali metals, for example lithium potassium or sodium, and $R^1$ is $C_1$–$C_4$-alkoxy.

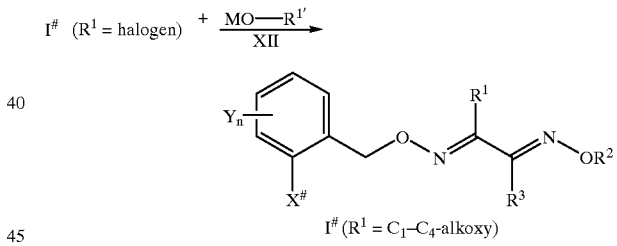

13. The reaction is normally carried out at from 20 to 120° C., preferably 20 to 80° C., in an inert organic solvent [cf. J. Org. Chem., 50 (1985), p. 993; Tetrahedron Lett., 35 (1994), p. 15].

Suitable solvents are ethers such as dioxane or tetrahydrofuran, nitriles such as acetonitrile, alcohols such as methanol, ethanol, n-propanol, isopropanol, n-butanol or tert-butanol, and dimethyl sulfoxide, dimethylformamide and dimethylacetamide. Mixtures of these can also be used.

In general, the starting materials are reacted with each other in equimolar amounts. It may be advantageous for the yield to employ XII in an excess based on I#.

Moreover, the compounds of the formula I where $R^1$ is $C_1$–$C_4$-alkoxy are obtained by reacting a benzyl compound of the formula IIa# with an oxime of the formula IIIe where $R^1$ is $C_1$–$C_4$-alkoxy under the conditions described in Section 5. for the reaction of IIa# with IIId.

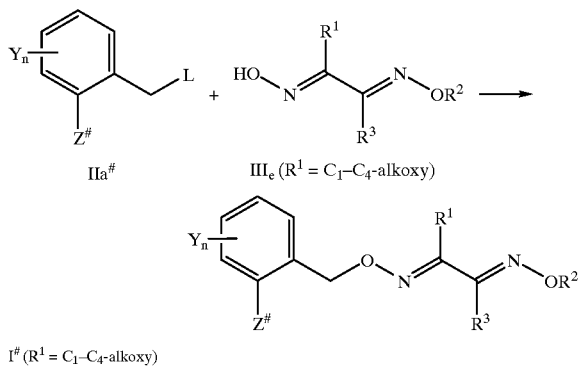

IIa#     IIIe (R$^1$ = C$_1$–C$_4$-alkoxy)

I# (R$^1$ = C$_1$–C$_4$-alkoxy)

14. The starting materials are generally reacted with each other in equimolar amounts. It may be advantageous for the yield to employ IIIe in an excess based on IIa#.

The oximes of the formula IIIe are obtained, for example, by reacting an oxime of the formula IIIF where R$^1$ is halogen with an alkoxide of the formula XII under the conditions described in Section 12. [cf. EP-A 158 153; U.S. Pat. No. 4,339,444], or they can be prepared in accordance with the literature cited.

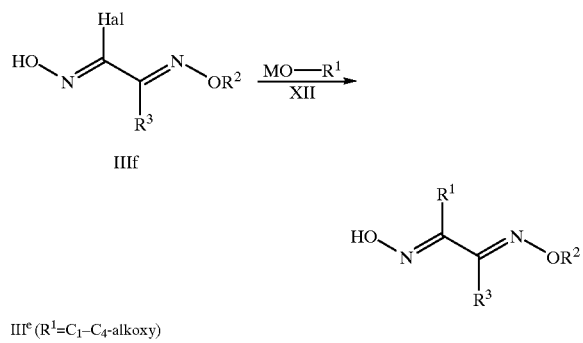

IIIf

IIIe (R$^1$=C$_1$–C$_4$-alkoxy)

The oximes of the formula IIIf are obtained, for example, by reacting a ketoxime of the formula IIIf' with a hydroxylamine ether of the formula VIII'.

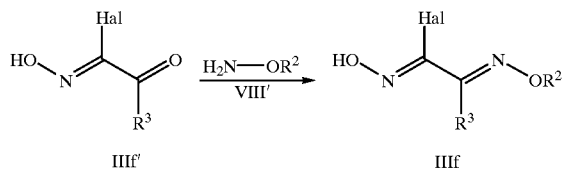

IIIf'     IIIf

Those ketoximes of the formula IIIf' which are not already known from the literature [cf. Ber. Dtsch. Chem. Ges. 88 (1955), p. 130; J. Org. Chem. (1987), p. 4570] can be prepared in accordance with the literature cited.

The reaction mixtures are worked up in the customary manner, for example by mixing with water, phase separation and, if appropriate, chromatographic purification of the crude products. Some of the intermediates and end products are obtained in the form of colorless or pale brown viscous oils, which are purified or freed from volatile components under reduced pressure and at a moderately elevated temperature. If the intermediates and end products are obtained as solids, they can also be purified by recrystallization or digestion.

When preparing the compounds I, their C=C. and C=N double bonds may entail E/Z isomer mixtures which can be separated into the individual compounds in the customary manner, for example by crystallization or chromatography.

If the synthesis yields isomer mixtures, however, a separation is generally not absolutely necessary, since some of the individual isomers can be converted into each other during processing for use or upon application (for example when exposed to light, acids or bases). Similar conversions may also take place after application, for example in the case of the treatment of plants in the treated plant, or in the harmful fungus or animal pest to be controlled.

With a view to the —N=CR$^1$—C(CR$^3$)=NOR$^2$ double bonds, the E,E isomers of the compounds I are generally preferred regarding their activity (configuration based on the radical —CH$_2$O— relative to the —C(CR$^3$)=NOR$^2$ group, or based on the radical —OR$^2$ relative to the —C(R$^1$)—N=OCH$_2$ group).

In the definitions of the symbols given in the above formulae, collective terms were used which generally represent the following substituents:

Halogen: fluorine, chlorine, bromine and iodine;

Alkyl: saturated, straight-chain or branched hydrocarbon radicals having 1 to 4 or 6 carbon atoms, eg. C$_1$–C$_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 4 or 6 carbon atoms (as mentioned above), it being possible for some or all of the hydrogen atoms in these groups to be replaced by halogen atoms as mentioned above, eg. C$_1$–C$_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro- 2,2-difluoroethyl, 2,2-dichloro-2-fluoroethyl, 2,2,2-trichloroethyl and pentafluoroethyl;

Alkaxy: straight-chain or branched alkyl groups having 1 to 6 carbon atoms (as mentioned above) which are bonded to the skeleton via an oxygen atom (—O—);

Alkenyl: unsaturated, straight-chain or branched hydrocarbon radicals having 3 to 4 carbon atoms and one double bond in any position, eg. C$_3$–C$_4$-alkenyl such as 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

Haloalkenyl: unsaturated, straight-chain or branched hydrocarbon radicals having 3 to 4 carbon atoms and one double bond in any position (as mentioned above), it being possible for some or all of the hydrogen atoms in these groups to be replaced by halogen atoms as mentioned above, in particular fluorine, chlorine and bromine;

Alkynyl: straight-chain or branched hydrocarbon groups having 3 to 4 carbon atoms and one triple bond in any position, eg. C$_3$–C$_4$-alkynyl such as ethynyl, 1-propynyl, 2-propynyl, 1-butynyl, 2-butynyl, 3-butynyl and 1-methyl-2-propynyl;

Haloalkynyl: unsaturated, straight-chain or branched hydrocarbon radicals having 3 to 4 carbon atoms and one triple bond in any position (as mentioned above), it being possible for some or all of the hydrogen atoms in these groups to be replaced by halogen atoms as mentioned above, in particular fluorine, chlorine and bromine;

Aryl: a mono- to trinuclear aromatic ring system containing 6 to 14 carbon ring members, eg. phenyl, naphthyl and anthracenyl;

Aryloxy: a mono- to trinuclear aromatic ring system (as mentioned above) which is bonded to the skeleton via an oxygen atom (—O—).

The addition "unsubstituted or substituted", when relating to the phenyl radical, is intended to express that this radical can be partially or fully halogenated [i.e. some or all of the hydrogen atoms of this radical can be replaced by identical or different halogen atoms as mentioned above (preferably fluorine, chlorine or bromine, in particular fluorine or chlorine)] and/or can have attached to it one to four (in particular one to three) of the following radicals: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio;

Heteroaryl:
 5-membered heteroaryl containing one to four nitrogen atoms or one to three nitrogen atoms and one sulfur or oxygen atom: 5-membered heteroaryl ring groups which, in addition to carbon atoms, can contain, as ring members, one to four nitrogen atoms or one to three nitrogen atoms and one sulfur or oxygen atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;
 benzo-fused 5-membered heteroaryl containing one to three nitrogen atoms or one nitrogen atom and one oxygen or sulfur atom: 5-membered heteroaryl ring groups which, in addition to carbon atoms, can contain, as ring members, one to four nitrogen atoms or one to three nitrogen atoms and one sulfur or oxygen atom and in which two adjacent carbon ring members or one nitrogen and one adjacent carbon ring member can be bridged by a buta-1,3-diene-1,4-diyl group;
 5-membered heteroaryl, bonded via nitrogen and containing one to four nitrogen atoms, or benzo-fused 5-membered heteroaryl, bonded via nitrogen and containing one to three nitrogen atoms: 5-membered heteroaryl ring groups which, in addition to carbon atoms, can contain, as ring members, one to four nitrogen atoms or one to three nitrogen atoms, respectively, and in which two adjacent carbon ring members or one nitrogen and one adjacent carbon ring member can be bridged by a buta-1,3-diene-1,4-diyl group, these rings being bonded to the skeleton via one of the nitrogen ring members;
 6-membered heteroaryl, containing one to three, or one to four, nitrogen atoms: 6-membered heteroaryl ring groups which, in addition to carbon atoms, can contain, as ring members, one to three, or one to four, nitrogen atoms, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

Heterocyclyl: 5- or 6-membered heterocycles (heterocyclyl) containing, in addition to carbon ring members, one to three nitrogen atoms and/or one oxygen or sulfur atom or one or two oxygen and/or sulfur atoms, eg. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-Piperidinyl, 3-Piperidinyl, 4-Piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-triazin-2-yl and 1,2,4-tetrahydrotriazin-3-yl.

Especially preferred compounds of the formula I with a view to their intended use are those where $R^a$ is $C_1$–$C_2$-alkyl or $C_1$–$C_2$-alkoxy.

Also preferred compounds of the formula I are those where n is zero (0).

Particularly preferred compounds of the formula I are those where $R^a$ is methyl or methoxy.

Particularly preferred compounds I are those where Z is a group B.

In addition, especially preferred compounds I are those where $R^1$ is methoxy.

Equally, especially preferred compounds I are those where $R^1$ is trifluoromethyl.

Besides, especially preferred compounds I are those where $R^1$ is chlorine.

Equally preferred compounds I are those where $R^1$ is $C_1$–$C_2$-haloalkyl.

Besides, especially preferred compounds I are those where $R^1$ is $C_1$–$C_2$-alkoxy.

Particularly especially preferred compounds I are those where $R^3$ is methyl.

Furthermore, especially preferred compounds I are those where $R^3$ is ethyl.

Also preferred compounds of the formula I are those where $R^3$ is $C_1$-$C_4$-alkoxy.

Particularly preferred compounds I are those where $R^3$ is ethoxy.

Equally preferred compounds I are those where $R^3$ is isopropoxy.

Besides, especially preferred compounds I are those where $R^3$ is trifluoromethyl.

Furthermore, especially preferred compounds I are those where $R^3$ is cyclopentyl.

In addition, especially preferred compounds I are those where $R^3$ is cyclohexyl.

Also, particularly preferred compounds I are those where $R^3$ is one of the following groups: phenyl or benzyl, both of which can be partially or fully halogenated in the aryl moiety and/or can have attached to them one to three of the following radicals: cyano, $C_1$-$C_4$-alkyl, $C_1$-$C_4$-haloalkyl, $C_1$-$C_4$-alkoxy and $C_1$-$C_4$-haloalkoxy.

Equally, especially preferred compounds I are those where $R^3$ is phenoxy which can be partially or fully halogenated and/or can have attached to it one to three of the following radicals: cyano, $C_1$-$C_4$-alkyl, $C_1$-$C_4$-haloalkyl, $C_1$-$C_4$-alkoxy and $C_1$-$C_4$-haloalkoxy.

Equally, especially preferred compounds I are those where $R^3$ is pyridyl.

In addition, especially preferred compounds I are those where $R^3$ is pyrimidinyl.

Furthermore preferred compounds are those of the formula I.1.

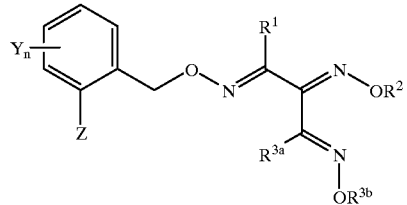

I.1

Equally, especially preferred compounds I.1 are those where $R^1$ is chlorine, $R^{3a}$ is methyl, $Y_n$ is hydrogen and $R^2$ is methyl or ethyl.

Besides, especially preferred compounds I.1 are those where $Y_n$ is 6-methyl.

Besides, preferred compounds are those of the formula I.2.

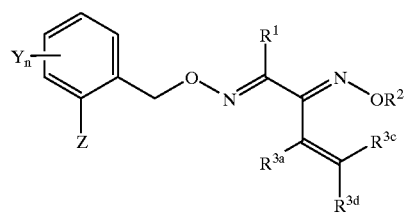

I.2

Equally preferred compounds I.2 are those where $R^{3d}$ is hydrogen.

Particularly preferred compounds I.2 are those where $R^{3a}$ and $Y_n$ are hydrogen and $R^2$ is methyl or ethyl.

In addition, especially preferred compounds I.2 are those where $R^{3a}$ is hydrogen, $R^2$ is methyl or ethyl and $Y_n$ is 6-methyl.

Particularly preferred with a view to their use are the compounds I which are compiled in the tables which follow.

In addition, the groups mentioned in the tables for one substituent are, per se and independently of the combination in which they are mentioned, an especially preferred embodiment of the substituent in question.

Table 1

Compounds of the formula IA where $R^a$ is methyl and the combination of the radicals $R^1$, $R^2$ and $R^3$ for each compound corresponds to one line of Table A

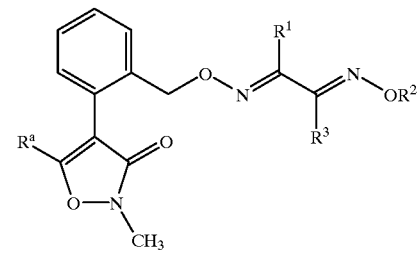

IA

Table 2

Compounds of the formula IB where $R^a$ is methyl and the combination of the radicals $R^1$, $R^2$ and $R^3$ for each compound corresponds to one line of Table A

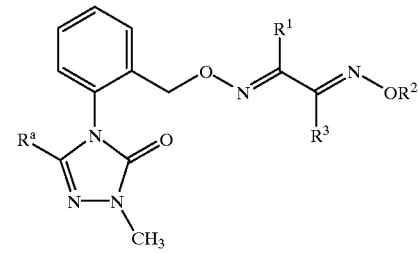

IB

Table 3

Compounds of the formula I.1A where $R^a$ is methyl, $R^1$ is chlorine and the combination of the radicals $R^2$, $R^{3a}$ and $R^{3b}$ for each compound corresponds to one line of Table B

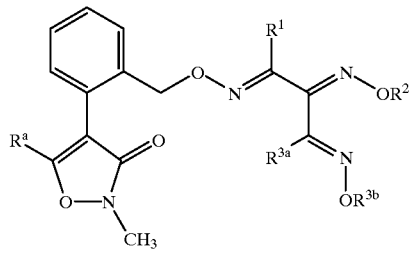

I.1A

Table 4

Compounds of the formula I.1A where $R^a$ is methoxy, $R^1$ is chlorine and the combination of the radicals $R^2$, $R^{3a}$ and $R^{3b}$ for each compound corresponds to one line of Table B Table 5

Compounds of the formula I.2A where $R^a$ and $R^2$ are methyl, $R^1$ is chlorine and the combination of the radicals $R^{3a}$, $R^{3c}$ and $R^{3d}$ for each compound corresponds to one line of Table C

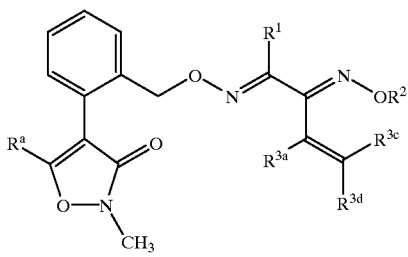

I.2A

Table 6

Compounds of the formula I.2A where $R^a$ is methoxy, $R^1$ is chlorine, $R^2$ is methyl and the combination of the radicals $R^{3a}$, $R^{3c}$ and $R^{3d}$ for each compound corresponds to one line of Table C Table 7

Compounds of the formula I.1B where $R^a$ is methyl, $R^1$ is chlorine and the combination of the radicals $R^2$, $R^{3a}$ and $R^d$ for each compound corresponds to one line of Table B

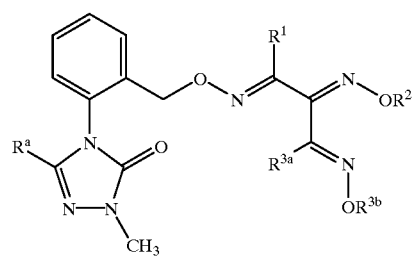

I.1B

Table 8

Compounds of the formula I.1B where $R^a$ is methoxy, $R^1$ is chlorine and the combination of the radicals $R^2$, $R^{3a}$ and $R^{3b}$ for each compound corresponds to one line of Table B Table 9

Compounds of the formula I.2B where $R^a$ and $R^2$ are methyl, $R^1$ is chlorine and the combination of the radicals $R^{3a}$, $R^{3c}$ and $R^{3d}$ for each compound corresponds to one line of Table C

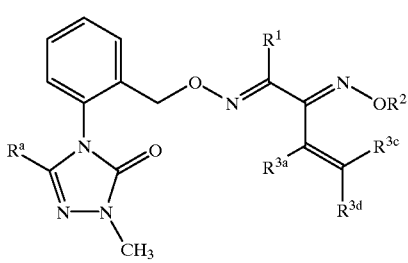

I.2B

Table 10

Compounds of the formula I.2B where $R^a$ is methoxy, $R^1$ is chlorine, $R^2$ is methyl and the combination of the radicals $R^{3a}$, $R^{3c}$ and $R^{3d}$ for each compound corresponds to one line of Table C Table 11

Compounds of the formula I.1A where $R^a$ is ethyl, $R^1$ is chlorine and the combination of the radicals $R^2$, $R^{3a}$ and $R^{3b}$ for each compound corresponds to one line of Table B Table 12

Compounds of the formula I.1A where $R^a$ is methoxy, $R^1$ is trifluoromethyl and the combination of the radicals $R^2$, $R^{3a}$ and $R^{3b}$ for each compound corresponds to one line of Table B Table 13

Compounds of the formula I.2A where $R^a$ and $R^2$ are methyl, $R^1$ is trifluoromethyl and the combination of the radicals $R^{3a}$, $R^{3c}$ and $R^{3d}$ for each compound corresponds to one line of Table C Table 14

Compounds of the formula I.2A where $R^a$ is methoxy, $R^1$ is trifluoromethyl, $R^2$ is methyl and the combination of the radicals $R^{3a}$, $R^{3c}$ and $R^{3d}$ for each compound corresponds to one line of Table C Table 15

Compounds of the formula I.1B where $R^a$ is ethyl, $R^1$ is trifluoromethyl and the combination of the radicals $R^2$, $R^{3a}$ and $R^d$ for each compound corresponds to one line of Table B Table 16

Compounds of the formula I.1B where $R^a$ is methoxy, $R^1$ is trifluoromethyl and the combination of the radicals $R^2$, $R^{3a}$ and $R^{3b}$ for each compound corresponds to one line of Table B Table 17

Compounds of the formula I.2B where $R^a$ and $R^2$ are methyl, $R^1$ is trifluoromethyl and the combination of the radicals $R^{3a}$, $R^{3c}$ and $R^{3d}$ for each compound corresponds to one line of Table C Table 18

Compounds of the formula I.2B where $R^a$ is methoxy, $R^1$ is trifluoromethyl and $R^2$ is methyl and the combination of the radicals $R^{3a}$, $R^{3c}$ and $R^{3d}$ for each compound corresponds to one line of Table C Table 19

Compounds of the formula I.1Ba where $R^a$ is methoxy, $R^1$ is chlorine and the combination of the radicals $R^2$, $R^{3a}$ and $R^{3b}$ for each compound corresponds to one line of Table B I.1Ba

[Structure I.1Ba]

Table 20

Compounds of the formula I.2Ba where $R^a$ is methoxy, $R^1$ is chlorine, $R^2$ is methyl and the combination of the radicals $R^{3a}$, $R^{3c}$ and $R^{3d}$ for each compound corresponds to one line of Table C I.2Ba

[Structure I.2Ba]

Table 21

Compounds of the formula I.1A where $R^a$ and $R^1$ are methoxy and the combination of the radicals $R^2$, $R^{3a}$ and $R^{3b}$ for each compound corresponds to one line of Table B Table 22

Compounds of the formula I.2A where $R^a$ and $R^2$ are methyl, $R^1$ is methoxy and the combination of the radicals $R^{3a}$, $R^{3c}$ and $R^{3d}$ for each compound corresponds to one line of Table C Table 23

Compounds of the formula I.2A where $R^a$ and $R^1$ are methoxy, $R^2$ is methyl and the combination of the radicals $R^{3a}$, $R^{3c}$ and $R^{3d}$ for each compound corresponds to one line of Table C Table 24

Compounds of the formula I.1B where $R^a$ is ethyl, $R^1$ is methoxy and the combination of the radicals $R^2$, $R^3$ and $R^d$ for each compound corresponds to one line of Table B Table 25

Compounds of the formula I.1B where $R^a$ and $R^1$ are methoxy and the combination of the radicals $R^2$, $R^{3a}$ and $R^{3b}$ for each compound corresponds to one line of Table B Table 26

Compounds of the formula I.2B where $R^a$ and $R^2$ are methyl, $R^1$ is methoxy and the combination of the radicals $R^{3a}$, $R^{3c}$ and $R^{3d}$ for each compound corresponds to one line of Table C Table 27

Compounds of the formula I.2B where $R^a$ and $R^1$ are methoxy, $R^2$ is methyl and the combination of the radicals $R^{3a}$, $R^{3c}$ and $R^{3d}$ for each compound corresponds to one line of Table C Table 28

Compounds of the formula I.3A where $R^a$ is methoxy, $R^2$ is methyl and the combination of the radicals $R^1$ and $R^{3e}$ for each compound corresponds to one line of Table D

I.3A

[Structure I.3A]

Table 29

Compounds of the formula I.3B where $R^a$ is methoxy, $R^2$ is methyl and the combination of the radicals $R^1$ and $R^{3e}$ for each compound corresponds to one line of Table D

I.3B

[Structure I.3B]

Table 30

Compounds of the formula I.3A where $R^a$ is methoxy, $R^2$ is ethyl and the combination of the radicals $R^1$ and $R^{3e}$ for each compound corresponds to one line of Table D Table 31

Compounds of the formula I.3B where $R^a$ is methoxy, $R^2$ is ethyl and the combination of the radicals $R^1$ and $R^{3e}$ for each compound corresponds to one line of Table D Table 32

Compounds of the formula I.3A where $R^a$ and $R^2$ are methyl and the combination of the radicals $R^1$ and $R^{3e}$ for each compound corresponds to one line of Table D Table 33

Compounds of the formula I.3B where $R^a$ and $R^2$ are methyl and the combination of the radicals $R^1$ and $R^{3e}$ for each compound corresponds to one line of Table D

TABLE A

| No. | R¹ | R² | R³ |
|---|---|---|---|
| A-1 | Cl | CH$_3$ | CH$_3$ |
| A-2 | Cl | CH$_3$ | CF$_3$ |
| A-3 | Cl | CH$_3$ | CH$_2$CH$_3$ |
| A-4 | Cl | CH$_3$ | CH$_2$CH$_2$CH$_3$ |
| A-5 | Cl | CH$_3$ | CH$_2$CH$_2$CH$_2$CH$_3$ |
| A-6 | Cl | CH$_3$ | CF$_2$CF$_3$ |
| A-7 | Cl | CH$_3$ | isopropyl |
| A-8 | Cl | CH$_3$ | tert-butyl |
| A-9 | Cl | CH$_3$ | cyclopropyl |
| A-10 | Cl | CH$_3$ | cyclopentyl |
| A-11 | Cl | CH$_3$ | cyclohexyl |
| A-12 | Cl | CH$_3$ | benzyl |
| A-13 | Cl | CH$_3$ | 2-pyridyl |
| A-14 | Cl | CH$_3$ | 3-pyridyl |
| A-15 | Cl | CH$_3$ | 4-pyridyl |
| A-16 | Cl | CH$_3$ | 3-CF$_3$-2-pyridyl |
| A-17 | Cl | CH$_3$ | 4-CF$_3$-2-pyridyl |
| A-18 | Cl | CH$_3$ | 5-CF$_3$-2-pyridyl |
| A-19 | Cl | CH$_3$ | 6-CF$_3$-2-pyridyl |
| A-20 | Cl | CH$_3$ | 3-Cl-5-CF$_3$-2-pyridyl |
| A-21 | Cl | CH$_3$ | 3-CF$_3$-5-Cl-2-pyridyl |
| A-22 | Cl | CH$_3$ | 2-pyrimidinyl |
| A-23 | Cl | CH$_3$ | 4-pyrimidinyl |
| A-24 | Cl | CH$_3$ | 2-oxazolyl |
| A-25 | Cl | CH$_3$ | 4-oxazolyl |
| A-26 | Cl | CH$_3$ | 3-isoxazolyl |
| A-27 | Cl | CH$_3$ | 5-isoxazolyl |
| A-28 | Cl | CH$_3$ | 3-pyrazolyl |
| A-29 | Cl | CH$_3$ | 4-pyrazolyl |
| A-30 | Cl | CH$_3$ | OCH$_3$ |
| A-31 | Cl | CH$_3$ | OCH$_2$CH$_3$ |
| A-32 | Cl | CH$_3$ | isopropoxy |
| A-33 | Cl | CH$_3$ | tert-butoxy |
| A-34 | Cl | CH$_3$ | OCH(CH$_3$)CH$_2$CH$_3$ |
| A-35 | Cl | CH$_3$ | OCH(CH$_2$CH$_3$)$_2$ |
| A-36 | Cl | CH$_3$ | OCH(CH$_3$)CH$_2$CH$_2$CH$_3$ |
| A-37 | Cl | CH$_3$ | cyclopentyloxy |
| A-38 | Cl | CH$_3$ | cyclohexyloxy |
| A-39 | Cl | CH$_3$ | phenyloxy |
| A-40 | Cl | CH$_3$ | benzyloxy |
| A-41 | Cl | CH$_3$ | OCH$_2$CF$_3$ |
| A-42 | Cl | CH$_2$CH$_3$ | CH$_3$ |
| A-43 | Cl | CH$_2$CH$_3$ | CF$_3$ |
| A-44 | Cl | CH$_2$CH$_3$ | CH$_2$CH$_3$ |
| A-45 | Cl | CH$_2$CH$_3$ | CH$_2$CH$_2$CH$_3$ |
| A-46 | Cl | CH$_2$CH$_3$ | CH$_2$CH$_2$CH$_2$CH$_3$ |
| A-47 | Cl | CH$_2$CH$_3$ | CF$_2$CF$_3$ |
| A-48 | Cl | CH$_2$CH$_3$ | isopropyl |
| A-49 | Cl | CH$_2$CH$_3$ | tert-butyl |
| A-50 | Cl | CH$_2$CH$_3$ | cyclopropyl |
| A-51 | Cl | CH$_2$CH$_3$ | cyclopentyl |
| A-52 | Cl | CH$_2$CH$_3$ | cyclohexyl |
| A-53 | Cl | CH$_2$CH$_3$ | benzyl |
| A-54 | Cl | CH$_2$CH$_3$ | 2-pyridyl |
| A-55 | Cl | CH$_2$CH$_3$ | 3-pyridyl |
| A-56 | Cl | CH$_2$CH$_3$ | 4-pyridyl |
| A-57 | Cl | CH$_2$CH$_3$ | 3-CF$_3$-2-pyridyl |
| A-58 | Cl | CH$_2$CH$_3$ | 4-CF$_3$-2-pyridyl |
| A-59 | Cl | CH$_2$CH$_3$ | 5-CF$_3$-2-pyridyl |
| A-60 | Cl | CH$_2$CH$_3$ | 6-CF$_3$-2-pyridyl |
| A-61 | Cl | CH$_2$CH$_3$ | 3-Cl-5-CF$_3$-2-pyridyl |
| A-62 | Cl | CH$_2$CH$_3$ | 3-CF$_3$-5-Cl-2-pyridyl |
| A-63 | Cl | CH$_2$CH$_3$ | 2-pyrimidinyl |
| A-64 | Cl | CH$_2$CH$_3$ | 4-pyrimidinyl |
| A-65 | Cl | CH$_2$CH$_3$ | 2-oxazolyl |
| A-66 | Cl | CH$_2$CH$_3$ | 4-oxazolyl |
| A-67 | Cl | CH$_2$CH$_3$ | 3-isoxazolyl |
| A-68 | Cl | CH$_2$CH$_3$ | 5-isoxazolyl |
| A-69 | Cl | CH$_2$CH$_3$ | 3-pyrazolyl |
| A-70 | Cl | CH$_2$CH$_3$ | 4-pyrazolyl |
| A-71 | Cl | CH$_2$CH$_3$ | OCH$_3$ |
| A-72 | Cl | CH$_2$CH$_3$ | OCH$_2$CH$_3$ |
| A-73 | Cl | CH$_2$CH$_3$ | isopropoxy |
| A-74 | Cl | CH$_2$CH$_3$ | tert-butoxy |
| A-75 | Cl | CH$_2$CH$_3$ | OCH(CH$_3$)CH$_2$CH$_3$ |
| A-76 | Cl | CH$_2$CH$_3$ | OCH(CH$_2$CH$_3$)$_2$ |
| A-77 | Cl | CH$_2$CH$_3$ | OCH(CH$_3$)CH$_2$CH$_2$CH$_3$ |
| A-78 | Cl | CH$_2$CH$_3$ | cyclopentyloxy |
| A-79 | Cl | CH$_2$CH$_3$ | cyclohexyloxy |
| A-80 | Cl | CH$_2$CH$_3$ | phenyloxy |
| A-81 | Cl | CH$_2$CH$_3$ | benzyloxy |
| A-82 | Cl | CH$_2$CH$_3$ | OCH$_2$CF$_3$ |
| A-83 | CF$_3$ | CH$_3$ | CH$_3$ |
| A-84 | CF$_3$ | CH$_3$ | CF$_3$ |
| A-85 | CF$_3$ | CH$_3$ | CH$_2$CH$_3$ |
| A-86 | CF$_3$ | CH$_3$ | CH$_2$CH$_2$CH$_3$ |
| A-87 | CF$_3$ | CH$_3$ | CH$_2$CH$_2$CH$_2$CH$_3$ |
| A-88 | CF$_3$ | CH$_3$ | CF$_2$CF$_3$ |
| A-89 | CF$_3$ | CH$_3$ | isopropyl |
| A-90 | CF$_3$ | CH$_3$ | tert-butyl |
| A-91 | CF$_3$ | CH$_3$ | cyclopropyl |
| A-92 | CF$_3$ | CH$_3$ | cyclopentyl |
| A-93 | CF$_3$ | CH$_3$ | cyclohexyl |
| A-94 | CF$_3$ | CH$_3$ | benzyl |
| A-95 | CF$_3$ | CH$_3$ | 2-pyridyl |
| A-96 | CF$_3$ | CH$_3$ | 3-pyridyl |
| A-97 | CF$_3$ | CH$_3$ | 4-pyridyl |
| A-98 | CF$_3$ | CH$_3$ | 3-CF$_3$-2-pyridyl |
| A-99 | CF$_3$ | CH$_3$ | 4-CF$_3$-2-pyridyl |
| A-100 | CF$_3$ | CH$_3$ | 5-CF$_3$-2-pyridyl |
| A-101 | CF$_3$ | CH$_3$ | 6-CF$_3$-2-pyridyl |
| A-102 | CF$_3$ | CH$_3$ | 3-Cl-5-CF$_3$-2-pyridyl |
| A-103 | CF$_3$ | CH$_3$ | 3-CF$_3$-5-Cl-2-pyridyl |
| A-104 | CF$_3$ | CH$_3$ | 2-pyrimidinyl |
| A-105 | CF$_3$ | CH$_3$ | 4-pyrimidinyl |
| A-106 | CF$_3$ | CH$_3$ | 2-oxazolyl |
| A-107 | CF$_3$ | CH$_3$ | 4-oxazolyl |
| A-108 | CF$_3$ | CH$_3$ | 3-isoxazolyl |
| A-109 | CF$_3$ | CH$_3$ | 5-isoxazolyl |
| A-110 | CF$_3$ | CH$_3$ | 3-pyrazolyl |
| A-111 | CF$_3$ | CH$_3$ | 4-pyrazolyl |
| A-112 | CF$_3$ | CH$_3$ | OCH$_3$ |
| A-113 | CF$_3$ | CH$_3$ | OCH$_2$CH$_3$ |
| A-114 | CF$_3$ | CH$_3$ | isopropoxy |
| A-115 | CF$_3$ | CH$_3$ | tert-butoxy |
| A-116 | CF$_3$ | CH$_3$ | OCH(CH$_3$)CH$_2$CH$_3$ |
| A-117 | CF$_3$ | CH$_3$ | OCH(CH$_2$CH$_3$)$_2$ |
| A-118 | CF$_3$ | CH$_3$ | OCH(CH$_3$)CH$_2$CH$_2$CH$_3$ |
| A-119 | CF$_3$ | CH$_3$ | cyclopentyloxy |
| A-120 | CF$_3$ | CH$_3$ | cyclohexyloxy |
| A-121 | CF$_3$ | CH$_3$ | phenyloxy |
| A-122 | CF$_3$ | CH$_3$ | benzyloxy |
| A-123 | CF$_3$ | CH$_3$ | OCH$_2$CF$_3$ |
| A-124 | CF$_3$ | CH$_2$CH$_3$ | CH$_3$ |
| A-125 | CF$_3$ | CH$_2$CH$_3$ | CF$_3$ |
| A-126 | CF$_3$ | CH$_2$CH$_3$ | CH$_2$CH$_3$ |
| A-127 | CF$_3$ | CH$_2$CH$_3$ | CH$_2$CH$_2$CH$_3$ |
| A-128 | CF$_3$ | CH$_2$CH$_3$ | CH$_2$CH$_2$CH$_2$CH$_3$ |
| A-129 | CF$_3$ | CH$_2$CH$_3$ | CF$_2$CF$_3$ |
| A-130 | CF$_3$ | CH$_2$CH$_3$ | isopropyl |
| A-131 | CF$_3$ | CH$_2$CH$_3$ | tert-butyl |
| A-132 | CF$_3$ | CH$_2$CH$_3$ | cyclopropyl |
| A-133 | CF$_3$ | CH$_2$CH$_3$ | cyclopentyl |
| A-134 | CF$_3$ | CH$_2$CH$_3$ | cyclohexyl |
| A-135 | CF$_3$ | CH$_2$CH$_3$ | benzyl |
| A-136 | CF$_3$ | CH$_2$CH$_3$ | 2-pyridyl |
| A-137 | CF$_3$ | CH$_2$CH$_3$ | 3-pyridyl |
| A-138 | CF$_3$ | CH$_2$CH$_3$ | 4-pyridyl |
| A-139 | CF$_3$ | CH$_2$CH$_3$ | 3-CF$_3$-2-pyridyl |
| A-140 | CF$_3$ | CH$_2$CH$_3$ | 4-CF$_3$-2-pyridyl |
| A-141 | CF$_3$ | CH$_2$CH$_3$ | 5-CF$_3$-2-pyridyl |
| A-142 | CF$_3$ | CH$_2$CH$_3$ | 6-CF$_3$-2-pyridyl |
| A-143 | CF$_3$ | CH$_2$CH$_3$ | 3-Cl-5-CF$_3$-2-pyridyl |
| A-144 | CF$_3$ | CH$_2$CH$_3$ | 3-CF$_3$-5-Cl-2-pyridyl |
| A-145 | CF$_3$ | CH$_2$CH$_3$ | 2-pyrimidinyl |
| A-146 | CF$_3$ | CH$_2$CH$_3$ | 4-pyrimidinyl |
| A-147 | CF$_3$ | CH$_2$CH$_3$ | 2-oxazolyl |
| A-148 | CF$_3$ | CH$_2$CH$_3$ | 4-oxazolyl |
| A-149 | CF$_3$ | CH$_2$CH$_3$ | 3-isoxazolyl |
| A-150 | CF$_3$ | CH$_2$CH$_3$ | 5-isoxazolyl |
| A-151 | CF$_3$ | CH$_2$CH$_3$ | 3-pyrazolyl |
| A-152 | CF$_3$ | CH$_2$CH$_3$ | 4-pyrazolyl |
| A-153 | CF$_3$ | CH$_2$CH$_3$ | OCH$_3$ |
| A-154 | CF$_3$ | CH$_2$CH$_3$ | OCH$_2$CH$_3$ |

TABLE A-continued

| No. | R$^1$ | R$^2$ | R$^3$ |
|---|---|---|---|
| A-155 | CF$_3$ | CH$_2$CH$_3$ | isopropoxy |
| A-156 | CF$_3$ | CH$_2$CH$_3$ | tert-butoxy |
| A-157 | CF$_3$ | CH$_2$CH$_3$ | OCH(CH$_3$)CH$_2$CH$_3$ |
| A-158 | CF$_3$ | CH$_2$CH$_3$ | OCH(CH$_2$CH$_3$)$_2$ |
| A-159 | CF$_3$ | CH$_2$CH$_3$ | OCH(CH$_3$)CH$_2$CH$_2$CH$_3$ |
| A-160 | CF$_3$ | CH$_2$CH$_3$ | cyclopentyloxy |
| A-161 | CF$_3$ | CH$_2$CH$_3$ | cyclohexyloxy |
| A-162 | CF$_3$ | CH$_2$CH$_3$ | phenyloxy |
| A-163 | CF$_3$ | CH$_2$CH$_3$ | benzyloxy |
| A-164 | CF$_3$ | CH$_2$CH$_3$ | OCH$_2$CF$_3$ |
| A-165 | OCH$_3$ | CH$_3$ | CH$_3$ |
| A-166 | OCH$_3$ | CH$_3$ | CF$_3$ |
| A-167 | OCH$_3$ | CH$_3$ | CH$_2$CH$_3$ |
| A-168 | OCH$_3$ | CH$_3$ | CH$_2$CH$_2$CH$_3$ |
| A-169 | OCH$_3$ | CH$_3$ | CH$_2$CH$_2$CH$_2$CH$_3$ |
| A-170 | OCH$_3$ | CH$_3$ | CF$_2$CF$_3$ |
| A-171 | OCH$_3$ | CH$_3$ | isopropyl |
| A-172 | OCH$_3$ | CH$_3$ | tert-butyl |
| A-173 | OCH$_3$ | CH$_3$ | cyclopropyl |
| A-174 | OCH$_3$ | CH$_3$ | cyclopentyl |
| A-175 | OCH$_3$ | CH$_3$ | cyclohexyl |
| A-176 | OCH$_3$ | CH$_3$ | benzyl |
| A-177 | OCH$_3$ | CH$_3$ | 2-pyridyl |
| A-178 | OCH$_3$ | CH$_3$ | 3-pyridyl |
| A-179 | OCH$_3$ | CH$_3$ | 4-pyridyl |
| A-180 | OCH$_3$ | CH$_3$ | 3-CF$_3$-2-pyridyl |
| A-181 | OCH$_3$ | CH$_3$ | 4-CF$_3$-2-pyridyl |
| A-182 | OCH$_3$ | CH$_3$ | 5-CF$_3$-2-pyridyl |
| A-183 | OCH$_3$ | CH$_3$ | 6-CF$_3$-2-pyridyl |
| A-184 | OCH$_3$ | CH$_3$ | 3-Cl-5-CF$_3$-2-pyridyl |
| A-185 | OCH$_3$ | CH$_3$ | 3-CF$_3$-5-Cl-2-pyridyl |
| A-186 | OCH$_3$ | CH$_3$ | 2-pyrimidinyl |
| A-187 | OCH$_3$ | CH$_3$ | 4-pyrimidinyl |
| A-188 | OCH$_3$ | CH$_3$ | 2-oxazolyl |
| A-189 | OCH$_3$ | CH$_3$ | 4-oxazolyl |
| A-190 | OCH$_3$ | CH$_3$ | 3-isoxazolyl |
| A-191 | OCH$_3$ | CH$_3$ | 5-isoxazolyl |
| A-192 | OCH$_3$ | CH$_3$ | 3-pyrazolyl |
| A-193 | OCH$_3$ | CH$_3$ | 4-pyrazolyl |
| A-194 | OCH$_3$ | CH$_3$ | OCH$_3$ |
| A-195 | OCH$_3$ | CH$_3$ | OCH$_2$CH$_3$ |
| A-196 | OCH$_3$ | CH$_3$ | isopropoxy |
| A-197 | OCH$_3$ | CH$_3$ | tert-butoxy |
| A-198 | OCH$_3$ | CH$_3$ | OCH(CH$_3$)CH$_2$CH$_3$ |
| A-199 | OCH$_3$ | CH$_3$ | OCH(CH$_2$CH$_3$)$_2$ |
| A-200 | OCH$_3$ | CH$_3$ | OCH(CH$_3$)CH$_2$CH$_2$CH$_3$ |
| A-201 | OCH$_3$ | CH$_3$ | cyclopentyloxy |
| A-202 | OCH$_3$ | CH$_3$ | cyclohexyloxy |
| A-203 | OCH$_3$ | CH$_3$ | phenyloxy |
| A-204 | OCH$_3$ | CH$_3$ | benzyloxy |
| A-205 | OCH$_3$ | CH$_3$ | OCH$_2$CF$_3$ |

TABLE B

| No. | R$^2$ | R$^{3a}$ | R$^{3b}$ |
|---|---|---|---|
| B-1 | CH$_3$ | H | CH$_3$ |
| B-2 | CH$_3$ | H | CH$_2$CH$_3$ |
| B-3 | CH$_3$ | H | CH$_2$CH$_2$CH$_3$ |
| B-4 | CH$_3$ | H | CH(CH$_3$)$_2$ |
| B-5 | CH$_3$ | H | C(CH$_3$)$_3$ |
| B-6 | CH$_3$ | H | CH$_2$CH=CH$_2$ |
| B-7 | CH$_3$ | H | CH$_2$C≡CH |
| B-8 | CH$_3$ | H | CH$_2$CH$_2$CH$_2$CH$_3$ |
| B-9 | CH$_3$ | CH$_3$ | CH$_3$ |
| B-10 | CH$_3$ | CH$_3$ | CH$_2$CH$_3$ |
| B-11 | CH$_3$ | CH$_3$ | CH$_2$CH$_2$CH$_3$ |
| B-12 | CH$_3$ | CH$_3$ | CH(CH$_3$)$_2$ |
| B-13 | CH$_3$ | CH$_3$ | C(CH$_3$)$_3$ |
| B-14 | CH$_3$ | CH$_3$ | CH$_2$CH=CH$_2$ |
| B-15 | CH$_3$ | CH$_3$ | CH$_2$C≡CH |
| B-16 | CH$_3$ | CH$_3$ | CH$_2$CH$_2$CH$_2$CH$_3$ |
| B-17 | CH$_3$ | CH$_2$CH$_3$ | CH$_3$ |
| B-18 | CH$_3$ | CH$_2$CH$_3$ | CH$_2$CH$_3$ |

TABLE B-continued

| No. | R$^2$ | R$^{3a}$ | R$^{3b}$ |
|---|---|---|---|
| B-19 | CH$_3$ | CH$_2$CH$_3$ | CH$_2$CH$_2$CH$_3$ |
| B-20 | CH$_3$ | CH$_2$CH$_3$ | CH(CH$_3$)$_2$ |
| B-21 | CH$_3$ | CH$_2$CH$_3$ | C(CH$_3$)$_3$ |
| B-22 | CH$_3$ | CH$_2$CH$_3$ | CH$_2$CH=CH$_2$ |
| B-23 | CH$_3$ | CH$_2$CH$_3$ | CH$_2$C≡CH |
| B-24 | CH$_3$ | CH$_2$CH$_3$ | CH$_2$CH$_2$CH$_2$CH$_3$ |
| B-25 | CH$_2$CH$_3$ | H | CH$_3$ |
| B-26 | CH$_2$CH$_3$ | H | CH$_2$CH$_3$ |
| B-27 | CH$_2$CH$_3$ | H | CH$_2$CH$_2$CH$_3$ |
| B-28 | CH$_2$CH$_3$ | H | CH(CH$_3$)$_2$ |
| B-29 | CH$_2$CH$_3$ | H | C(CH$_3$)$_3$ |
| B-30 | CH$_2$CH$_3$ | H | CH$_2$CH=CH$_2$ |
| B-31 | CH$_2$CH$_3$ | H | CH$_2$C≡CH |
| B-32 | CH$_2$CH$_3$ | H | CH$_2$CH$_2$CH$_2$CH$_3$ |
| B-33 | CH$_2$CH$_3$ | CH$_3$ | CH$_3$ |
| B-34 | CH$_2$CH$_3$ | CH$_3$ | CH$_2$CH$_3$ |
| B-35 | CH$_2$CH$_3$ | CH$_3$ | CH$_2$CH$_2$CH$_3$ |
| B-36 | CH$_2$CH$_3$ | CH$_3$ | CH(CH$_3$)$_2$ |
| B-37 | CH$_2$CH$_3$ | CH$_3$ | C(CH$_3$)$_3$ |
| B-38 | CH$_2$CH$_3$ | CH$_3$ | CH$_2$CH=CH$_2$ |
| B-39 | CH$_2$CH$_3$ | CH$_3$ | CH$_2$C≡CH |
| B-40 | CH$_2$CH$_3$ | CH$_3$ | CH$_2$CH$_2$CH$_2$CH$_3$ |
| B-41 | CH$_2$CH$_3$ | CH$_2$CH$_3$ | CH$_3$ |
| B-42 | CH$_2$CH$_3$ | CH$_2$CH$_3$ | CH$_2$CH$_3$ |
| B-43 | CH$_2$CH$_3$ | CH$_2$CH$_3$ | CH$_2$CH$_2$CH$_3$ |
| B-44 | CH$_2$CH$_3$ | CH$_2$CH$_3$ | CH(CH$_3$)$_2$ |
| B-45 | CH$_2$CH$_3$ | CH$_2$CH$_3$ | C(CH$_3$)$_3$ |
| B-46 | CH$_2$CH$_3$ | CH$_2$CH$_3$ | CH$_2$CH=CH$_2$ |
| B-47 | CH$_2$CH$_3$ | CH$_2$CH$_3$ | CH$_2$C≡CH |
| B-48 | CH$_2$CH$_3$ | CH$_2$CH$_3$ | CH$_2$CH$_2$CH$_2$CH$_3$ |

TABLE C

| No. | R$^{3a}$ | R$^{3c}$ | R$^{3d}$ |
|---|---|---|---|
| C-1 | H | H | H |
| C-2 | H | H | CH$_3$ |
| C-3 | H | H | CH$_2$CH$_3$ |
| C-4 | H | H | CH$_2$CH$_2$CH$_3$ |
| C-5 | H | H | CH(CH$_3$)$_2$ |
| C-6 | H | H | C(CH$_3$)$_3$ |
| C-7 | H | H | CH$_2$—C$_6$H$_5$ |
| C-8 | H | H | CH=CH—CH$_3$ |
| C-9 | H | H | C$_6$H$_5$ |
| C-10 | H | H | 4-Cl—C$_6$H$_4$ |
| C-11 | H | H | 4-F—C$_6$H$_4$ |
| C-12 | H | CH$_3$ | CH$_3$ |
| C-13 | H | CH$_3$ | CH$_2$CH$_3$ |
| C-14 | H | CH$_3$ | CH$_2$CH$_2$CH$_3$ |
| C-15 | H | CH$_3$ | CH(CH$_3$)$_2$ |
| C-16 | H | CH$_3$ | C(CH$_3$)$_3$ |
| C-17 | H | CH$_3$ | CH$_2$—C$_6$H$_5$ |
| C-18 | H | CH$_3$ | C$_6$H$_5$ |
| C-19 | H | CH$_3$ | 4-Cl—C$_6$H$_4$ |
| C-20 | H | CH$_3$ | 4-F—C$_6$H$_4$ |
| C-21 | CH$_3$ | H | H |
| C-22 | CH$_3$ | H | CH$_3$ |
| C-23 | CH$_3$ | H | CH$_2$CH$_3$ |
| C-24 | CH$_3$ | H | CH$_2$CH$_2$CH$_3$ |
| C-25 | CH$_3$ | H | CH(CH$_3$)$_2$ |
| C-26 | CH$_3$ | H | C(CH$_3$)$_3$ |
| C-27 | CH$_3$ | H | CH$_2$—C$_6$H$_5$ |
| C-28 | CH$_3$ | H | CH=CH—CH$_3$ |
| C-29 | CH$_3$ | H | C$_6$H$_5$ |
| C-30 | CH$_3$ | H | 4-Cl—C$_6$H$_4$ |
| C-31 | CH$_3$ | H | 4-F—C$_6$H$_4$ |
| C-32 | CH$_3$ | CH$_3$ | H |
| C-33 | CH$_3$ | CH$_3$ | CH$_3$ |
| C-34 | CH$_3$ | CH$_3$ | CH$_2$CH$_3$ |
| C-35 | H | CH$_3$ | H |
| C-36 | H | CH$_2$CH$_3$ | H |
| C-37 | H | CH$_2$CH$_2$CH$_3$ | H |
| C-38 | H | CH(CH$_3$)$_2$ | H |
| C-39 | H | C(CH$_3$)$_3$ | H |

TABLE C-continued

| No. | $R^{3a}$ | $R^{3c}$ | $R^{3d}$ |
|---|---|---|---|
| C-40 | H | $CH_2-C_6H_5$ | H |
| C-41 | H | $CH=CH-CH_3$ | H |
| C-42 | H | $C_6H_5$ | H |
| C-43 | H | $4-Cl-C_6H_4$ | H |
| C-44 | H | $4-F-C_6H_4$ | H |
| C-45 | H | $CH_2CH_3$ | $CH_3$ |
| C-46 | H | $CH_2CH_2CH_3$ | $CH_3$ |
| C-47 | H | $CH(CH_3)_2$ | $CH_3$ |
| C-48 | H | $C(CH_3)_3$ | $CH_3$ |
| C-49 | H | $CH_2-C_6H_5$ | $CH_3$ |
| C-50 | H | $C_6H_5$ | $CH_3$ |
| C-51 | H | $4-Cl-C_6H_4$ | $CH_3$ |
| C-52 | H | $4-F-C_6H_4$ | $CH_3$ |
| C-53 | $CH_3$ | $CH_2CH_3$ | H |
| C-54 | $CH_3$ | $CH_2CH_2CH_3$ | H |
| C-55 | $CH_3$ | $CH(CH_3)_2$ | H |
| C-56 | $CH_3$ | $C(CH_3)_3$ | H |
| C-57 | $CH_3$ | $CH_2-C_6H_5$ | H |
| C-58 | $CH_3$ | $CH=CH-CH_3$ | H |
| C-59 | $CH_3$ | $C_6H_5$ | H |
| C-60 | $CH_3$ | $4-Cl-C_6H_4$ | H |
| C-61 | $CH_3$ | $4-F-C_6H_4$ | H |
| C-62 | $CH_3$ | $CH_2CH_3$ | $CH_3$ |

TABLE D

| No. | $R^1$ | $R^{3e}$ |
|---|---|---|
| D-1 | Cl | H |
| D-2 | Cl | 2-F |
| D-3 | Cl | 3-F |
| D-4 | Cl | 4-F |
| D-5 | Cl | 2-Cl |
| D-6 | Cl | 3-Cl |
| D-7 | Cl | 4-Cl |
| D-8 | Cl | $2-CH_3$ |
| D-9 | Cl | $3-CH_3$ |
| D-10 | Cl | $4-CH_3$ |
| D-11 | Cl | $4-CF_3$ |
| D-12 | Cl | 4-Br |
| D-13 | Cl | $2,4-F_2$ |
| D-14 | Cl | $2,4-Cl_2$ |
| D-15 | Cl | $3,4-F_2$ |
| D-16 | Cl | $3,4-F_2$ |
| D-17 | Cl | $3,5-F_2$ |
| D-18 | Cl | $4-OCH_3$ |
| D-19 | $CF_3$ | H |
| D-20 | $CF_3$ | 2-F |
| D-21 | $CF_3$ | 3-F |
| D-22 | $CF_3$ | 4-F |
| D-23 | $CF_3$ | 2-Cl |
| D-24 | $CF_3$ | 3-Cl |
| D-25 | $CF_3$ | 4-Cl |
| D-26 | $CF_3$ | $2-CH_3$ |
| D-27 | $CF_3$ | $3-CH_3$ |
| D-28 | $CF_3$ | $4-CH_3$ |
| D-29 | $CF_3$ | $4-CF_3$ |
| D-30 | $CF_3$ | 4-Br |
| D-31 | $CF_3$ | $2,4-F_2$ |
| D-32 | $CF_3$ | $2,4-Cl_2$ |
| D-33 | $CF_3$ | $3,4-F_2$ |
| D-34 | $CF_3$ | $3,4-F_2$ |
| D-35 | $CF_3$ | $3,5-F_2$ |
| D-36 | $CF_3$ | $4-OCH_3$ |
| D-37 | $OCH_3$ | H |
| D-38 | $OCH_3$ | 2-F |
| D-39 | $OCH_3$ | 3-F |
| D-40 | $OCH_3$ | 4-F |
| D-41 | $OCH_3$ | 2-Cl |
| D-42 | $OCH_3$ | 3-Cl |
| D-43 | $OCH_3$ | 4-Cl |
| D-44 | $OCH_3$ | $2-CH_3$ |
| D-45 | $OCH_3$ | $3-CH_3$ |
| D-46 | $OCH_3$ | $4-CH_3$ |
| D-47 | $OCH_3$ | $4-CF_3$ |
| D-48 | $OCH_3$ | 4-Br |
| D-49 | $OCH_3$ | $2,4-F_2$ |
| D-50 | $OCH_3$ | $2,4-Cl_2$ |
| D-51 | $OCH_3$ | $3,4-F_2$ |
| D-52 | $OCH_3$ | $3,4-F_2$ |
| D-53 | $OCH_3$ | $3,5-F_2$ |
| D-54 | $OCH_3$ | $4-OCH_3$ |

The compounds I are suitable as fungicides. They are distinguished by an outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,
Botrytis cinerea (gray mold) on strawberries, vegetables, ornamentals and grapevines,
Cercospora arachidicola on peanuts,
Erysiphe cichoracearum and Sphaerotheca fuliginea on cucurbits,
Erysiphe graminis (powdery mildew) on cereals,
Fusarium and Verticillium species on various plants,
Helminthosporium species on cereals,
Mycosphaerella species on bananas and peanuts,
Phytophthora infestans on potatoes and tomatoes,
Plasmopara viticola on grapevines,
Podosphaera leucotricha on apples,
Pseudocercosporella herpotrichoides on wheat and barley,
Pseudocercosporella species on hops and cucumbers,
Puccinia species on cereals,
Pyricularia oryzae on rice,
Rhizoctonia species on cotton, rice and turf,
Septoria nodorum on wheat,
Uncinula necator on grapevines,
Ustilago species on cereals and sugar cane, and
Venturia species (scab) on apples and pears.

Moreover, the compounds I are suitable for controlling harmful fungi such as Paecilomyces variotii in the protection of materials (eg. wood, paper, paint dispersions, fibers and fabrics) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

Moreover, the compounds of the formula I are suitable for efficiently controlling animal pests from the classes of the insects, arachnids and nematodes. They can be employed in crop protection and in the hygiene, stored-product and veterinary sector for controlling animal pests. In particular, they are suitable for controlling the following animal pests:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria,* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa,* thrips (Thysanoptera), eg. *Frankliniella fusca, Frankliniella occidentalis, Frankliniella tritici, Scirtothrips citri, Thrips oryzae, Thrips palmi* and *Thrips tabaci,* hymenopterans (Hymenoptera), eg. *Athalia rosae, Atta cephalotes, Atta sexdens, Atta texana, Hoplocampa minuta, Hoplocampa testudinea, Monomorium pharaonis, Solenopsis geminata* and *Solenopsis invicta,* heteropterans (Heteroptera), eg. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* homopterans (Homoptera), eg. *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii,* termites (Isoptera), eg. *Calotermes flavicollis, Leucotermes flavipes, Reticulitermes lucifugus* und *Termes natalensis,* orthopterans (Orthoptera), eg. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus,*

Arachnoidea, such as arachnids (Acarina), eg. *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus,*

*Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae,* nematodes such as root knot nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The rate of application of active ingredient for controlling animal pests is from 0.1 to 2.0, preferably 0.2 to 1.0, kg/ha under field conditions.

The compounds I can be converted into the customary formulations, eg. solutions, emulsions, suspensions, dusts, powders, pastes and granules. The use form depends on the particular purpose; it is intended to ensure in each case a fine and uniform distribution of the compound according to the invention.

The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are examples of formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; it is intended to ensure in each case the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water. The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

Various types of oils, herbicides, fungicides, other pesticides, or bactericides may be added to the active ingredients, if appropriate just immediately prior to use (tank mix). These agents can be admixed with the agents according to the invention in a weight ratio of 1:10 to 10:1.

In the use form as fungicides, the compositions according to the invention can also be present together with other active ingredients, eg. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]- quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane;

Amines such as 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, (8-(1,1-dimethylethyl)-N-ethyl-N-propyl-1,4-dioxaspiro[4.5]decane-2-methaneamine;

Azoles such as 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]1-H-1,2,4-triazole, 1-[2-(2,4-dichlorophenyl)pentyl]-1H-1,2,4-triazole, 2,4'-difluoro-a-(1H-1,2,4-triazolyl-1-methyl)benzhydryl alcohol, 1-((bis-(4-fluorophenyl)methylsilyl)methyl)-1H-1,2,4-triazole, 1-[2RS,4RS;2RS,4SR)-4-bromo-2-(2,4-dichlorophenyl)tetrahydrofuryl]-1H-1,2,4-triazole, 2-(4-chlorophenyl)-3-cyclopropyl-1-(1H-1,2,4-triazol-1-yl)butan-2-ol (+)-4-chloro-4-[4-methyl-2-(1H-1,2,4-triazolyl-1-ylmethyl)-1,3-dioxolan-2-yl]phenyl 4-chlorophenyl ether, (E)-(R,S)-1-(2,4-dichlorophenyl)-4,4-dimethyl-2-(1H-1,2,4-tri-azol-1-yl)pent-1-en-3-ol, 4-(4-chlorophenyl)-2-phenyl-2-(1H-1,2,4,-triazolylmethyl)

butyronitrile, 3-(2,4-dichlorophenyl)-6-fluoro-2-(1H-1, 2,4-triazol-1-yl)quinazolin-4-(3H)-one, (R,S)-2-(2,4-dichlorophenyl)-1-H-1,2,4-triazol-1-yl)hexan-2-ol, (1RS,5RS;1RS,5SR)-5-(4-chlorobenzyl)-2,2-dimethyl-1-(1R-1,2,4-triazol-1-ylmethyl) cyclopentanol, (R,S)-1-(4-chlorophenyl)-4,4-dimethyl-3-(1H-1,2,4-triazol-1-ylmethyl)pentan-3-ol, (+)-2-(2, 4-dichlorophenyl)-3-(1H-1,2,4-triazolyl)propyl 1,1,2, 2-tetrafluoroethyl ether, (E)-1-[1-(4-chloro-2-trifluoromethyl)phenyl]imino)-2-propoxyethyl-1H-imidazole, 2-(4-chlorophenyl)-2-(1H-1,2,4-triazol-1-ylmethyl)hexanonitrile;

α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;

strobilurins such as methyl E-methoxyimino-[α-(o-tolyloxy)-o-tolyl]acetate, methyl E-2-{2-[6-(2-cyanophenoxy)pyrimidin-4-yloxy]-phenyl}-3-methoxyacrylate, N-methyl-E-methoxy-imino-[(α-(2-phenoxyphenyl)]acetamide, N-methyl E-methoxyimino-[α-(2,5-dimethylphenoxy)-o-tolyl] acetamide;

anilinopyrimidines such as N-(4,6-dimethylpyrimidin-2-yl)aniline, N-[4-methyl-6-(1-propynyl)pyrimidin-2-yl] aniline, N-[4-methyl-6-cyclopropylpyrimidin-2-yl] aniline;

phenylpyrroles such as 4-(2,2-difluoro-1,3-benzodioxol-4-yl)pyrrole-3-carbonitrile;

cinnamamides such as 3-(4-chlorophenyl)-3-(3,4-dimethoxyphenyl)acryloylmorpholine;

and a variety of fungicides such as dodecylguanidine acetate, 3-[3-(3,5-dimethyl-2-oxycyclohexyl)-2-hydroxyethyl]glutarimide, N-methyl-, N-ethyl-(4-trifluoromethyl,-2-[3',4,-dimethoxyphenyl]benzamide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-amino-butyrolactone, DL-N-(2,6-dimethylphenyl)-N-(phenylacetyl)-alanine methyl ester, 5-methyl-5-vinyl-3-(3,5-dichlorophenyl)-2,4-dioxo-1,3-oxazolidine, 3-[3,5-dichlorophenyl(5-methyl-5-methoxymethyl]-1, 3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, N-(3-chloro-2,6-dinitro-4-trifluoromethylphenyl)-5-trifluoromethyl-3-chloro-2-aminopyridine.

SYNTHESIS EXAMPLES

With due modification of the starting compounds, the protocols shown in the synthesis examples below were used for obtaining further compounds I. The resulting compounds, together with physical data, are listed in the Tables which follow.

Example 1

Preparation of

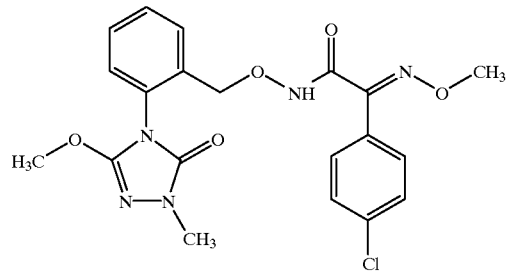

2.3 g of α-methoxyimino-N-hydroxy-4-chlorophenylacetamide and 3 g of 4-[2-bromomethyl) phenyl]-2,4-dihydro-5-methoxy-2-methyl-3H-1,2,4-triazol-3-one [cf. WO-A 97/00,612] dissolved in 50 ml of dimethylformamide, were treated with 1.8 g of methanolic sodium methoxide solution (30% strength). After the mixture had been stirred for approximately 20 hours at 20 to 25° C., it was poured into ice-water and extracted with ethyl acetate, and the organic phases were dried and concentrated. After chromatography on silica gel, 2.0 g of the title compound were obtained.

$^1$H NMR (CDCl$_3$): δ=2.45 (s); 3.2 (s); 3.9 (d); 4.8 (m); 7.3–7.6 ppm (m).

Example 2

Preparation of

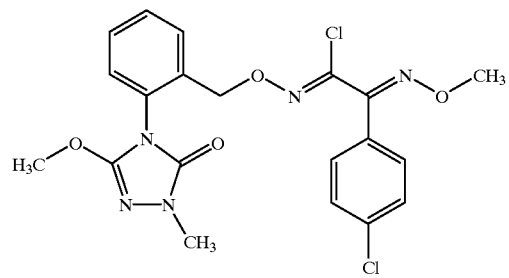

The solution of 2 g of the product obtained in Example 1 in 100 ml of acetonitrile was treated with 5.9 g of triphenylphosphine and 3.5 g of tetrachloromethane and refluxed for 72 hours. Then, the solvent was distilled off and the residue was chromatographed on silica gel. This gave 260 mg of the title compound.

$^1$H NMR (CDCl$_3$): δ=3.4 (d); 3.9 (s); 4.0 (s); 5.2 (q); 7.0–7.5 ppm (m).

Example 3

Preparation of

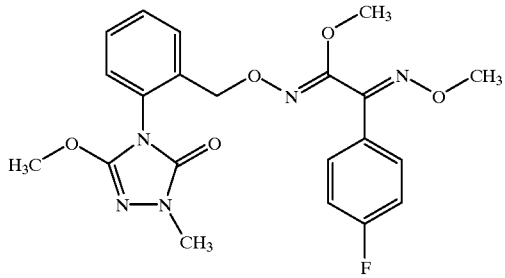

0.5 g of methyl α-methoxyimino-4-fluorophenylhydroximate, dissolved in 20 ml of dimethylformamide, was treated with 58 mg of sodium hydride. After the dissolution had been stirred for 30 minutes at approximately 20 to 25° C., 0.52 g of 4-[2-bromomethyl)phenyl]-2,4-dihydro-5-methoxy-2-methyl-3H-1,2,4-triazol-3-one was added. After the mixture had been stirred for 2 hours at approximately 20 to 25° C., it was poured into ice-water and extracted with methyl tert-butyl ether. The combined organic phases were washed with dilute sodium hydroxide solution, dilute hydrochloric acid and saturated $NaHCO_3$ solution and then dried and concentrated. This gave 0.8 g of the title compound.

$^1$H NMR ($CDCl_3$): δ=3.4 (5); 3.7 (5); 3.8 (5); 4.0 (5); 5.0 (8); 7.0–7.6 ppm (m).

Examples of the Action Against Harmful Fungi

The fungicidal action of the compounds of the formula I was demonstrated by the following experiments:

The active ingredients were formulated separately or jointly as a 10% emulsion in a mixture of 70% by weight of cyclohexanone, 20% by weight of Nekanil® LN (Lutensol® AP6, wetter with emulsifying and dispersant action based on ethoxylated alkylphenols) and 10% by weight of Wettol® EM (nonionic emulsifier based on ethoxylated castor oil) and diluted with water to give the desired concentration.

Use Example 1

Activity Against Powdery Mildew of Wheat

Leaves of potted wheat seedlings cv. "Frühgold" were sprayed to run off point with an aqueous preparation of active compound which had been prepared from a stock solution comprising 10% of active compound, 63% of cyclohexanone and 27% of emulsifier and, 24 hours after the spray coating had dried on, dusted with spores of powdery mildew of wheat (Erysiphe graminis forma specialis tritici). The test plants were subsequently placed in a greenhouse at from 20 to 24° C. and a relative atmospheric humidity of 60 to 90%. After 7 days, the extent of mildew development was determined visually as % infection of the total leaf area.

Use Example 2

Activity Against Puccinia Recondita on Wheat (brown rust of wheat)

Leaves of potted wheat seedlings cv. "Frühgold" were dusted with spores of brown rust (*Puccinia recondite*). The pots were then kept for 24 hours in a chamber of high atmospheric humidity (90 to 95%) at 20 to 22° C. During this time, the spores germinated and the germinal tubes penetrated into the leaf tissue. The next day, the infected plants were sprayed to run off point with an aqueous preparation of active compound which had been prepared from stock solution comprising 10% of active compound, 63% of cyclohexanone and 27% of emulsifier. After the spray coating had dried on, the test plants were cultivated in a greenhouse at temperatures from 20 to 22° C. and at 65 to 70% relative atmospheric humidity for 7 days. The extent of the rust fungus development on the leaves was then determined.

In these tests, the plants which had been treated with 63 ppm of the compounds of Examples 2 and 3 showed at most 15% infection, whereas the untreated plants were infected to 80 and 85%, respectively.

Examples of the Action Against Animal Pests

The action of the compounds of the formula I against animal pests was demonstrated by the following experiments:

The active ingredients were formulated a. as a 0.1% strength solution in acetone or b. as a 10% emulsion in a mixture of 70% by weight of cyclohexanone, 20% by weight of Nekanil® LN (Lutensol® AP6, wetter with emulsifying and dispersant action based on ethoxylated alkylphenols) and 10% by weight of Wettol® EM (nonionic emulsifier based on ethoxylated castor oil)

and diluted with to give the desired concentration, using acetone in the case of a. and water in the case of b.

After the experiments had been concluded, in each case the lowest concentration at which the compounds still caused an 80 to 100% inhibition or mortality was determined in comparison with untreated controls (limit or minimal concentration).

We claim:

1. An imino-substituted phenyl compound of the formula I

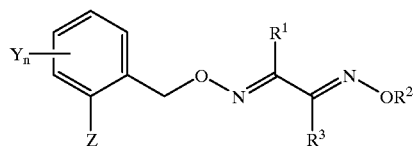

where the substituents have the following meanings:

Z is a group A or B

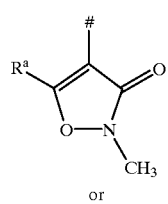

or

-continued

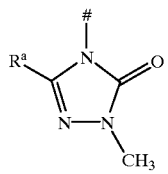

B where signifies the bond with the phenyl ring and $R^a$ is halogen, $C_1$–$C_4$-alkyl or $C_1$–$C_4$-alkoxy;

Y is halogen, $C_1$–$C_4$-alkyl, $C_1$–$C_4$-haloalkyl or $C_1$–$C_4$-alkoxy;

n is 0, 1 or 2, it being possible for the radicals Y to be different if n=2;

$R^1$ is halogen, $C_1$–$C_4$-haloalkyl or $C_1$–$C_4$-alkoxy;

$R^2$ is $C_1$–$C_4$-alkyl, $C_1$–$C_4$-haloalkyl, $C_3$–$C_4$-alkenyl, $C_3$–$C_4$-haloalkenyl, $C_3$–$C_4$-alkynyl or $C_3$–$C_4$-haloalkynyl;

$R^3$ is cyano, $C_1$–$C_6$-alkyl, $C_1$–$C_6$-haloalkyl, $C_1$–$C_6$-alkoxy, $C_3$–$C_6$-cycloalkoxy, $C_2$–$C_6$-alkoxyalkyl;

$C_3$–$C_6$-cycloalkyl, which can be partially or fully halogenated and/or have attached to it one to three $C_1$–$C_4$-alkyl groups;

phenyl which, in turn, can be partially or fully halogenated and/or have attached to it one to three of the following groups: cyano, nitro, $C_1$–$C_4$-alkyl, $C_1$–$C_4$-haloalkyl, $C_1$–$C_4$-alkoxy and $C_1$–$C_4$-haloalkoxy; aryl, aryloxy or arylmethylene which can be partially or fully halogenated in the aryl moiety and/or can have attached to it one to three of the following radicals: cyano, nitro, $C_1$–$C_4$-alkyl, $C_1$–$C_4$-haloalkyl, $C_1$–$C_4$-alkoxy and $C_1$–$C_4$-haloalkoxy;

unsubstituted or substituted heteroaryl, unsubstituted or substituted heterocyclyl, $C(R^{3a})$=N—$OR^{3b}$ or $C(R^{3a})$=$CR^{3c}R^{3d}$, where $R^{3a}$, $R^{3b}$, $R^{3c}$, $R^{3d}$ independently of one another are hydrogen, $C_1$–$C_6$-alkyl or unsubstituted or substituted phenyl.

2. A process for the preparation of a compound of the formula I as claimed in claim 1 where $R^1$ is halogen, which comprises converting a benzyl compound of the formula IIa

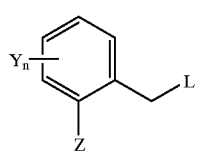

IIa where L is a nucleophilically exchangeable group with an oxime of the formula IIIb

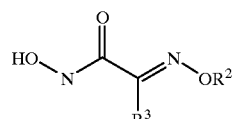

IIIb into a hydroxamic ester of the formula IVa

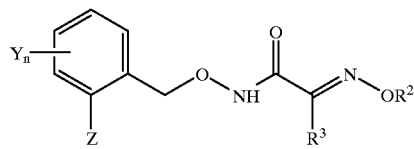

IVa and reacting IVa with a halogenating agent.

3. A process for the preparation of the compound of the formula I.1

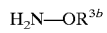

I.1 as claimed in claim 1 where $R^{3a}$ and $R^{3b}$ independently of one another are hydrogen and methyl, which comprises reacting a carbonyl compound of the formula X

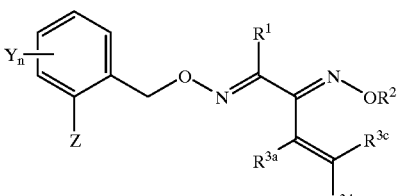

X with a hydroxylamine ether of the formula VIII $H_2N$—$OR^{3b}$     VIII.

4. A process for the preparation of a compound of the formula I.2

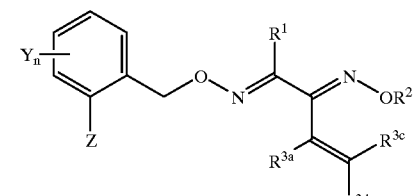

I.2 as claimed in claim 1, which comprises reacting a benzyl compound of the formula IIa

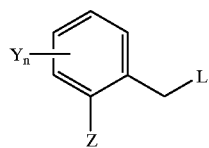

where L is a nucleophilically exchangeable group, with an oxime of the formula V

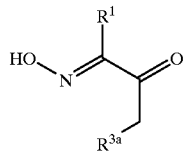

and converting, by means of halogenation, the resulting oxime ether of the formula VI

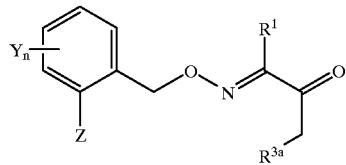

into the halogen compound of the formula VII

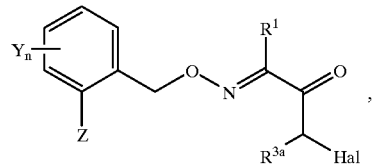

reacting VII with a hydroxylamine ether of the formula VIII'

to give the bisoxime ether of the formula IX

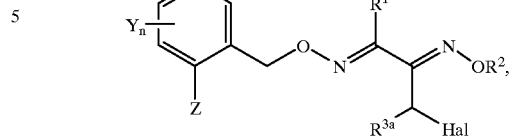

oxidizing IX to give the carbonyl compound of the formula X and reacting X with a phosphorus reagent following the principles of a Wittig reaction.

5. A composition which is suitable for controlling animal pests or harmful fungi, comprising a solid or liquid carrier and a compound of the formula I as claimed in claim 1.

6. A method of controlling harmful fungi, which comprises treating the fungi or the materials, plants, the soil or seeds to be protected against fungal infection with an effective amount of a compound of the formula I as claimed in claim 1.

7. A method of controlling animal pests, which comprises treating the animal pests or the materials, plants, the soil or seed to be protected against them with an effective amount of a compound of the formula I as claimed in claim 1.

8. The compound of formula I defined in claim 1, wherein $R^1$ is $C_1$–$C_2$-alkoxy, $C_1$–$C_2$-haloalkyl, or chlorine.

9. The compound of formula I defined in claim 1, wherein n is 0.

10. The compound of formula I defined in claim 1, wherein $R^3$ is $C_1$–$C_4$-alkoxy, trifluoromethyl, cyclopentyl, cyclohexyl, pyridyl, pyrimidyl, phenyl or benzyl, each of which is unsubstituted or partially or fully halogenated in the aryl moiety, or carries, optionally in addition to halogen, from one to three of the following radicals: cyano, $C_1$–$C_4$-alkyl, $C_1$–$C_4$-haloalkyl, $C_1$–$C_4$-alkoxy and $C_1$–$C_4$-haloalkoxy; phenoxy which is unsubstituted or partially or fully halogenated, or carries, optionally in addition to halogen, from one to three of the following radicals: cyano, $C_1$–$C_4$-alkyl, $C_1$–$C_4$-haloalkyl, $C_1$–$C_4$-alkoxy and $C_1$–$C_4$-haloalkoxy.

* * * * *